(12) United States Patent
Snyder

(10) Patent No.: US 7,747,551 B2
(45) Date of Patent: Jun. 29, 2010

(54) REDUCTION OF CLASSIFICATION ERROR RATES AND MONITORING SYSTEM USING AN ARTIFICIAL CLASS

(75) Inventor: David Snyder, Bainbridge Island, WA (US)

(73) Assignee: NeuroVista Corporation, Seattle, WA (US)

( * ) Notice: Subject to any disclaimer, the term of this patent is extended or adjusted under 35 U.S.C. 154(b) by 553 days.

(21) Appl. No.: 11/679,135

(22) Filed: Feb. 26, 2007

(65) Prior Publication Data
US 2008/0208781 A1 Aug. 28, 2008

Related U.S. Application Data

(60) Provisional application No. 60/902,580, filed on Feb. 21, 2007.

(51) Int. Cl.
*G06F 15/18* (2006.01)
(52) U.S. Cl. ...................................................... 706/20
(58) Field of Classification Search .................... 706/20
See application file for complete search history.

(56) References Cited

U.S. PATENT DOCUMENTS

| | | | | |
|---|---|---|---|---|
| 5,092,343 | A * | 3/1992 | Spitzer et al. | 600/515 |
| 5,995,651 | A * | 11/1999 | Gelenbe et al. | 382/156 |
| 6,507,829 | B1 * | 1/2003 | Richards et al. | 706/45 |
| 6,561,992 | B1 * | 5/2003 | Eberhart et al. | 600/595 |
| 6,596,501 | B2 * | 7/2003 | Roth | 435/7.21 |
| 6,852,743 | B1 * | 2/2005 | Ojima et al. | 514/364 |
| 7,043,474 | B2 * | 5/2006 | Mojsilovic et al. | 707/6 |
| 7,070,817 | B2 * | 7/2006 | Kuppam | 424/734 |
| 7,113,819 | B2 * | 9/2006 | Hamilton et al. | 600/511 |
| 7,202,243 | B2 * | 4/2007 | Hendrix et al. | 514/243 |
| 7,357,934 | B2 * | 4/2008 | Donovan et al. | 424/239.1 |
| 7,427,601 | B2 * | 9/2008 | Stoehr | 514/19 |
| 7,428,323 | B2 * | 9/2008 | Hillman | 382/128 |
| 7,544,470 | B2 * | 6/2009 | Boeke | 435/6 |
| 2009/0030403 | A1 * | 1/2009 | Leyde | 604/890.1 |

OTHER PUBLICATIONS

Artificial Neural Network for the Analysis of Electroencephalogram Nayak, K.P.; Padmashree, T.K.; Rao, S.N.; Cholayya, N.U.; Intelligent Sensing and Information Processing, 2006. ICISIP 2006. Fourth International Conference on Oct. 15, 2006-Dec. 18, 2006 pp. 170-173 Digital Object Identifier 10.1109/ICISIP.2006.4286089.*
Epileptic Seizure Detection using AR Model on EEG Signals Mousavi, S.R.; Niknazar, M.; Vahdat, B.V.; Biomedical Engineering Conference, 2008. CIBEC 2008. Cairo International Dec. 18-20, 2008 pp. 1-4 Digital Object Identifier 10.1109/CIBEC.2008. 4786067.*

(Continued)

*Primary Examiner*—Michael B Holmes
(74) *Attorney, Agent, or Firm*—Fenwick & West LLP

(57) ABSTRACT

Systems and methods for enhancing the accuracy of classifying a measurement by providing an artificial class. Seizure prediction systems may employ a classification system including an artificial class and a user interface for signaling uncertainty in classification when a measurement is classified in the artificial class.

21 Claims, 11 Drawing Sheets

OTHER PUBLICATIONS

A comparison of algorithms for detection of spikes in the electroencephalogram Pang, C.C.C.; Upton, A.R.M.; Shine, G.; Kamath, M.V.; Biomedical Engineering, IEEE Transactions on vol. 50, Issue 4, Apr. 2003 pp. 521-526 Digital Object Identifier 10.1109/TBME.2003.809479.*

Processing EEG signals for Clinical Interpretation in Seizure-Suspected Patients Lay-Ekuakille, A.; Vendramin, G.; Trotta, A.; De Rinaldis, M.; Trabacca, A.; Medical Measurement and Applications, 2007. MEMEA '07. IEEE International Workshop on May 4-5, 2007 pp. 1-4 Digital Object Identifier 10.1109/MEMEA.2007.4285157.*

Adjouadi, M. et al., "A New Mathematical Approach Based on Orthogonal Operators for the Detection of Interictal Spikes in Epileptogenic Data," Presented at Rocky Mountain Bioengineering Symposium & International ISA Biomedical Sciences Instrumentation Symposium, 2004, pp. 175-180.

Adjouadi, M. et al., "Interictal Spike Detection Using the Walsh Transform," IEEE Transactions on Biomedical Engineering, May 2004, pp. 868-872, vol. 51, No. 5.

Adjouadi, M. et al., "Detection of Interictal Spikes and Artifactual Data Through Orthogonal Transformations," Journal of Clinical Neurophysiology, Feb. 2005, pp. 53-64, vol. 22, No. 1.

Aksenova, T.I. et al., "On-Line Disharmony Detection for Early Prediction of Epilepsy Seizure Onset," 2003, 2 pages.

Aksenova, T.I. et al., "Nonparametric On-Line Detection of Changes in Signal Spectral Characteristics for Early Prediction of Epilepsy Seizure Onset," Journal of Automation and Information Sciences, 2004, pp. 35-45, vol. 36, No. 8.

Andrzejak, R.G. et al., "Testing the Null Hypothesis of the Nonexistence of a Preseizure State," Physical Review, 2003, pp. 1-4, The American Physical Society, vol. 67, No. 010901(R).

Andrzejak, R.G. et al., "Bivariate Surrogate Techniques: Necessity, Strengths, and Caveats," Physical Review, 2003, pp. 1-15, The American Physical Society, vol. 68, No. 066202.

Aschenbrenner-Scheibe, R. et al., "How Well Can Epileptic Seizures be Predicted? An Evaluation of a Nonlinear Method," Brain, Sep. 23, 2003, pp. 2616-2626, vol. 126.

Bangham, A.D. et al., "Diffusion of Univalet Ions Across the Lamellae of Swollen Phospholipids," J. Mol. Biol., 1965, pp. 238-252, vol. 13.

Baruchi, I. et al., "Functional Holography of Recorded Neuronal Networks Activity," Neuroinformatics, 2004, pp. 333-352, vol. 4.

Baruchi, I. et al., Functional Holography of Complex Networks Activity—From Cultures to the Human Brain, Complexity, 2005, pp. 38-51, vol. 10, No. 3, Wiley Periodicals, Inc.

Ben-Hur, A. et al., "Detecting Stable Clusters Using Principal Component Analysis," in Methods in Molecular Biology, 2003 pp. 1-23.

Bergey, G.K. et al., "Epileptic Seizures are Characterized by Changing Signal Complexity," Clinical Neurophysiology, 2001, pp. 1-9, Elsevier.

Betterton, P. et al., "Determining State of Consciousness from the Intracranial Electroencephalogram (IEEG) for Seizure Prediction," Proceedings of the 22$^{nd}$ IASTED International Conference Modelling, Identification and Control, Feb. 10-13, 2003, Innsbruck, Austria, pp. 313-317.

Bhattacharya, J. et al., "Enhanced Phase Synchrony in the Electroencephalograph γ Band for Musicians While Listening to Music," Physical Review, 2001, pp. 1-4, The American Physical Society, vol. 64, No. 012902.

Boley, D. et al., "Training Support Vector Machine Using Adaptive Clustering," Proceedigns of the Fourth SIAM International Conference on Data Mining, 2004,12 pages.

Burges, C.J.C., "A Tutorial on Support Vector Machines for Pattern Recognition," Data Mining and Knowledge Discovery, 1998, pp. 121-167, vol. 2, Kluwer Academic Publishers.

Cao, Y. et al., "Detecting Dynamical Changes in Time Series Using the Permutation Entropy," Physical Review, 2004, pp. 1-7, vol. 70, No. 046217.

Carretero-González, R. et al., "Scaling and Interleaving of Subsystem Lyapunov Exponents for Spatio-Temporal Systems," Chaos, Jun. 1999, pp. 466-482, vol. 9, No. 2.

Casdagli, M.C. et al., "Nonlinear Analysis of Mesial Temporal Lobe Seizures Using a Surrogate Data Technique," Epilepsia, Annual Meeting of the American Epilepsy Society, Baltimore, Maryland, Dec. 1-6, 1995, p. 142, vol. 36, Suppl. 4.

Casdagli, M.C. et al., "Characterizing Nonlinearity in Invasive EEG Recordings from Temporal Lobe Epilepsy," Physica D, Dec. 15, 1996, pp. 1-17, vol. 99, Issues 2-3.

Casdagli, M.C. et al., "Non-Linearity in Invasive EEG Recordings from Patients with Temporal Lobe Epilepsy," Electroencephalography and Clinical Neurophysiology, Feb. 1997, pp. 1-10, vol. 102, Issue 2.

Cerf, R. et al., "Criticality and Synchrony of Fluctuations in Rhythmical Brain Activity: Pretransitional Effectsin Epileptic Patients," Biological Cybernetics, Mar. 30, 2004, pp. 239-255, vol. 903.

Chaovalitwongse, W. et al., "EEG Classification in Epilepsy," Jun. 30, 2004, Annals.tex, pp. 1-32, vol. 2, No. 37, Kluwer Academic Publishers, Netherlands.

Chaovalitwongse, W. et al., "Performance of a Seizure Warning Algorithm Based on the Dynamics of Intracranial EEG," Epilepsy Research, 2003, pp. 1-46, vol. 64, Issue 3.

Chaovalitwongse, W.A. et al., "Reply to Comments on "Performance of a Seizure Warning Algorithm Based on the Dynamics of Intracranial EEG" by Winterhalder, M., Schelter, B., Achulze-Bonhage, A., Timmer, J.," Epilepsy Research, Jul. 31, 2006, pp. 82-84, vol. 72, Elsevier.

Chávez, M. et al., "Spatio-Temporal Dynamics Prior to Neocortical Seizures: Amplitude Versus Phase Couplings," IEEE Transactions on Biomedical Engineering, May 2003, pp. 571-583, vol. 50 No. 5.

Chrichton, M., "The Terminal Man," 1972, pp. 21-24, 32-33, 70-81, Alfred A. Knopf, New York.

D'Alessandro, M. et al., "A Multi-Feature and Multi-Channel Univariate Selection Process for Seizure Prediction," Clinical Neurophysiology, 2005, pp. 506-516, vol. 116.

D'Alessandro, M. et al., "Epileptic Seizure Prediction Using Hybrid Feature Selection Over Multiple Intracranial EEG Electrode Contacts: A Report of Four Patients," IEEE Transactions on Biomedical Engineering, May 2003, pp. 603-615, vol. 50, No. 5.

Drury, I. et al., "Seizure Prediction Using Scalp Electroencephalogram," Experimental Neurology, 2003, pp. S9-S18, vol. 184.

Ebersole, J.S., "In Search of Seizure Prediction: A Critique," Clinical Neurophysiology, 2005, pp. 489-492, vol. 116.

Ebersole, J.S., "Functional Neuroimaging with EEG Source Models to Localize Epileptogenic Foci Noninvasively," Neuorology, Available at http://www.uchospitals.edu/pdf/uch.sub.--001471.pdf, Accessed Feb. 28, 2006, 3 pages.

Elbert, T. et al., "Chaos and Physiology: Deterministic Chaos in Excitable Cell Assemblies," Physiological Reviews, Jan. 1994, pp. 1-47, vol. 74, No. 1.

Elger, C.E. et al., "Nonlinear EEG Analysis and Its Potential Role in Epileptology," Epilepsia, 2000, pp. S34-S38, vol. 41, Suppl. 3.

Elger, C.E. et al., "Short Communication—Seizure Prediction by Non-Linear Time Series Analysis of Brain Electrical Activity," European Journal of Neuroscience, 1998, pp. 786-789, vol. 10.

Esteller, R. et al., "Continuous Energy Variation During the Seizure Cycle: Towards an On-Line Accumulated Energy," Clinical Neurophysiology, Jan. 22, 2005, pp. 517-526, vol. 116.

Esteller, R. et al., "Feature Parameter Optimization for Seizure Detection/Prediction," IntelliMedix, Inc., [online] [Retrieved on Oct. 31, 2005] Retrieved from the Internet<URL:http://66.102.7.104/search?q=cache:4he0GuwtlacJ:icsl.m... re%2520Detection%2520Prediction.doc+intellimedix&hl=en>.

Esteller, R. et al., "A Comparison of Waveform Fractal Dimension Algorithms," IEEE Transactions on Circuits and Systems—I: Fundamental Theory and Applications, Feb. 2001, pp. 177-183, vol. 48, No. 2.

Faul, S. et al., "An Evaluation of Automated Neonatal Seizure Detection Methods," Clinical Neurophysiology, 2005, pp. 1533-1541, vol. 116.

Fein, G. et al., "Common Reference Coherence Data are Confounded by Power and Phase Effects," Electroencephalography and Clinical Neurophysiology, 1988, pp. 581-584, vol. 69, Elsevier Scientific Publishers, Ireland, Ltd.

Fell, J. et al., "Linear Inverse Filtering Improves Spatial Separation of Nonlinear Brain Dynamics: A Simulation Study," Journal of Neuroscience Methods, 2000, pp. 49-56, vol. 98, Elsevier.

Firpi, H. et al., "Epileptic Seizure Detection by Means of Genetically Programmed Artifical Features," GECCO '05, Jun. 25-29, 2005, pp. 461-466.

Fisher, R.S. "Reassessment: Vagus Nerve Stimulation for Epilepsy," American Academy of Neurology, 1999, [online] [Retrieved on Apr. 14, 2006] Retrieved from the Internet<URL:www.neurology.org>.

Franaszczuk, P.J. et al., "An Autoregressive Method for the Measurement of Synchronization of Interictal and Ictal EEG Signals," Biological Cybernetics, 1999, pp. 3-9, vol. 81, Springer-Verlag.

Gardner, A.B., "A Novelty Detection Approach to Seizure Analysis from Intracranial EEG," Dissertation, Georgia Institute of Technology, Apr. 2004, pp. 1-146.

Geva, A.B. et al., "Forecasting Generalized Epileptic Seizures from the EEG Signal by Wavelet Analysis and Dynamic Unsupervised Fuzzy Clustering," IEEE Transactions on Biomedical Engineering, Oct. 1998, pp. 1205-1216, vol. 45, No. 10.

Gigola, S. et al., "Prediction of Epileptic Seizures Using Accumulated Energy in a Multiresolution Framework," Journal of Neuroscience Methods, 2004, pp. 107-111, vol. 138, Elsevier.

Guyon, I. et al., "Multivariate Non-Linear Feature Selection with Kernel Multiplicative Updates and Gram-Schmidt Relief," To appear in the proceedings of the BISC FLINT-CIBI 2003 workshop, Berkeley, Dec. 2003, pp. 1-11.

Guyon, I. et al., "An Introduction to Variable and Feature Selection," Journal of Machine Learning Research, Mar. 2003, pp. 1157-1182, vol. 3.

Harrison, M.A. et al., "Accumulated Energy Revisited," Clinical Neurophysiology, 2005, pp. 527-531, vol. 116, Elsevier.

Harrison, M.A.F. et al., "Correlation Dimension and Integral do not Predict Epileptic Seizures," Chaos, 2005, pp. 1-15, vol. 15, No. 033106, American Institute of Physics.

Hearst, M.A., "Support Vector Machines," IEEE Intelligent Systems, Jul./Aug. 1998, pp. 18-28.

Hively, L.M. et al., "Detecting Dynamical Change in Nonlinear Time Series," Physics Letters A, Jul. 19, 1999, pp. 103-114, vol. 258, Elsevier.

Hively, L.M. et al., "Epileptic Seizure Forewarning by Nonlinear Techniques," Oak Ridge National Laboratory, Nov. 2000, 40 pages.

Hively, L.M. et al., "Channel-Consistent Forewarning of Epileptic Events from Scalp EEG," IEEE Transactions on Biomedical Engineering, May 2003, pp. 584-593, vol. 50, No. 5.

Hjorth, B., "Source Derivation Simplifies Topographical EEG Interpretation," Am.J. EEG Techol., 1980, pp. 121-132, vol. 20.

Hsu, C-W. et al., "A Practical Guide to Support Vector Classification," 2003, pp. 1-12.

Huynh, J.A., "Evaluation of Gene Selection Using Support Vector Machine Recursive Feature Elimination," Internship Report, May 26, 2004, pp. 1-25.

Huynh, J., "Evaluation of Gene Selection Using Support Vector Machine Recursive Feature Elimination," Powerpoint Presentation, 2004, 41 pages.

Iasemidis, L.D. et al., "Modelling of EcoG in Temporal Lobe Epilepsy," Proceedings of the $25^{th}$ Rocky Mountain Bioengineering Symposium, Colorado Springs, CO, 1988, pp. 1-12.

Iasemidis, L.D. et al., "Phase Space Topography and the Lyapunov Exponent of Electrocorticograms in Partial Seizures," Brain Topography, Mar. 1990, pp. 187-201, vol. 2, No. 3.

Iasemidis, L.D. et al., "Localizing Preictal Temporal Lobe Spike Foci Using Phase Space Analysis," Abstracts of the XIIth International Congress of Electroencephalography and Clinical Neurophysiology, Rio de Janeiro, Brazil, Jan. 14-19, 1990, pp. S63-S64, vol. 75, No. 1, Elsevier Scientific Publishers Ireland, Ltd.

Iasemidis, L.D. et al., "Long-Time-Scale Temporo-Spatial Patterns of Entrainment of Preictal Electrocorticopraphic Data in Human Temporal Lobe Epilepsy," Epilepsia, Sep./Oct. 1990, p. 621, vol. 31, No. 5.

Iasemidis, L.D. et al., "The Evolution with Time of the Spatial Distribution of the Largest Lyapunov Exponent on the Human Epileptic Cortex," in Mearsuring Chaos in the Human Brain, 1991, Eds. D. Duke et al., pp. 1-27.

Iasemidis, L.D. et al., "The Use of Dynamical Analysis of EEG Frequency Content in Seizure Prediction," Society Proceedings, American EEG Society, 1993 Annual Meeting, New Orleans, LA, Oct. 11-12, 1993, Electroencephalography and Clinical Neurophysiology, 1994, p. 39P, vol. 91.

Iasemidis, L.D. et al., "Quantification of Hidden Time Dependencies in the EEG within the Framework of Nonlinear Dynamics," in Nonlinear Dynamical Analysis of the EEG, 1993, Eds. B.H. Jansen et al., pp. 30-47.

Iasemidis, L.D. et al., "Time Dependencies in Partial Epilpesy," Epilepsia, Abstracts from the Annual Meeting of the American Epileptic Society, Miami, FL, Dec. 5-8, 1993, pp. 130-131, vol. 34, Suppl. 6.

Iasemidis, L.D. et al., "Time Dependencies in the Occurrences of Epileptic Seizures," Epilepsy Research, 1994, pp. 81-94, vol. 17, Elsevier.

Iasemidis, L.D. et al., "Spatiotemporal Evolution of Dynamical Measures Precedes Onset of Mesial Temporal Lobe Seizures," Epilepsia, Abstracts from the Annual Meeting of the American Epilepsy Society, New Orleans, LA, Dec. 2-8, 1994, p. 133, vol. 35, Suppl. 8.

Iasemidis, L.D. et al., "Spatiotemporal Dynamics of Human Epileptic Seizures," in Proceedings of the $3^{rd}$ Experimental Chaos Conference, 1996, R.G. Harrison et al. (Eds.), pp. 26-30.

Iasemidis, L.D. et al., "Chaos Theory and Epilepsy," 1996, pp. 1-13.

Iasemidis, L.D. et al., "Detection of the Preictal Transition State in Scalp-Sphenoidal EEG Recordings," Journal of Clinical Neurophysiology, Sep. 1996, pp. 443-444, vol. 13, No. 5.

Iasemidis, L.D. et al., "Preictal Entrainment of a Critical Cortical Mass is a Necessary Condition for Seizure Occurrence," Epilepsia, Abstracts from the Annual Meeting of the American Epilepsy Society, San Francisco, CA, Dec. 7-10, 1996, p. 90, vol. 37, Suppl. 5.

Iasemidis, L.D. et al., "Spatiotemporal Transition to Epileptic Seizures: A Nonlinear Dynamical Analysis of Scalp and Intracranial EEG Recordings," Spatiotemporal Models in Biological and Artificial Systems, F.L. Silva et al. (Eds.), 1997, pp. 81-88, IOS Press.

Iasemidis, L.D. et al.,, "Epileptogenic Focus Localization by Dynamic Analysis of Interictal Periods of EEG in Patients with Temporal Lobe Epilepsy," Epilepsia, Abstracts from the Annual Meeting of the American Epilepsy Society, Boston, MA, Dec. 7-10, 1997, p. 213, vol. 38, Suppl. 8.

Iasemidis, L.D. et al., "Preictal-Postictal Versus Postictal Analysis for Epileptogenic Focus Localization," J. Clin. Neurophysiol., 1997, p. 144, vol. 14.

Iasemidis, L.D. et al., "Dynamical Interaction of the Epileptogenic Focus with Extrafocal Sites in Temporal Lobe Epilepsy," Annals of Neurology, Sep. 1997, p. 429, vol. 42, No. 3.

Iasemidis, L.D. et al., "Nonlinear Dynamics of Electrocorticographic Data in Temporal Lobe Epilepsy," Journal of Clinical Neurophysiology, 1988, p. 339, vol. 5, No. 4, Raven Press.

Iasemidis, L.D. et al., "Automated Seizure Prediction Paradigm," Epilepsia, Abstracts from the Annual Meeting of the American Epilepsy Society, San Diego, CA, Dec. 6-9, 1998, p. 207, vol. 39, Suppl. 6.

Iasemidis, L.D. et al., "Measurement and Quantification of Spatio-Temporal Dynamics of Human Epileptic Seizures," in Nonlinear Signal Processing in Medicine, M. Akay (Ed.), 1999, pp. 1-27, IEEE Press.

Iasemidis, L.D. et al., "Quadratic Binary Programming and Dynamical System Approach to Determine the Predictability of Epileptic Siezures," Journal of Combinatorial Optimization, 2001, pp. 9-26, vol. 5, Kluwer Academic Publishers, Netherlands.

Iasemidis, L.D., "Epileptic Seizure Prediction and Control," IEEE Transactions on Biomedical Engineering, May 2003, pp. 549-558, vol. 50, No. 5.

Iasemidis, L.D. et al., "Adaptive Epileptic Seizure Prediction System," IEEE Transactions on Biomedical Engineering, May 2003, pp. 616-627, vol. 50, No. 5.

Iasemidis, L.D. et al., "Comment on Inability of Lyapunov Exponents to Predict Epileptic Seizures," Physical Review Letters, Jan. 14, 2005, 1 page, PRL 94, 019801.

Iasemidis, L.D. et al., "Long-Term Prospective On-Line Real-Time Seizure Prediction," Clinical Neurphysiology, 2005, pp. 532-544, vol. 116.

Jerger, K.K. et al., "Early Seizure Detection," Journal of Clinical Neurphysiology, 2001, pp. 259-268, vol. 18, No. 3.

Jerger, K.K. et al., "Multivariate Linear Discrimination of Seizures," Clinical Neurophysiology, 2005, pp. 545-551, vol. 116.

Jouny, C.C. et al., "Characterization of Epileptic Seizure Dynamics Using Gabor Atom Density," Clinical Neurophysiology, 2003, pp. 426-437, vol. 114.

Jouny, C.C. et al., "Signal Complexity and Synchrony of Epileptic Seizures: Is There an Identifiable Preictal Period?" Clinical Neurophysiology, 2005, pp. 552-558, vol. 116.

Kapiris, P.G. et al., "Similarities in Precursory Features in Seismic Shocks and Epileptic Seizures," Europhysics Letters, Feb. 15, 2005, pp. 657-663, vol. 69, No. 4.

Katz, A. et al., "Does Interictal Spiking Change Prior to Seizures?" Electroencephalography and Clinical Neurophysiology, 1991, pp. 153-156, vol. 79, Elsevier Scientific Publishers Ireland Ltd.

Kerem, D.H. et al., "Forecasting Epilepsy from the Heart Rate Signal," Medical & Biological Engineering & Computing, 2005, pp. 230-239, vol. 43.

Khalilov, I. et al. "Epilptogenic Actions of GABA and Fast Oscillations in the Developing Hippocampus," Neuron, Dec. 8, 2005, pp. 787-796, vol. 48, Elsevier Inc.

Korn, H. et al., "Is there Chaos in the Brain? II. Experimental Evidence and Related Models," C.R. Biologies, 2003, pp. 787-840, vol. 326.

Kraskov, A., "Synchronization and Interdependence Measures and their Applications to the Electroencephalogram of Epilepsy Patients and Clustering of Data," Dissertation (PhD Thesis), Publication Series of the John von Neumann Institute for Computing (NIC), NIC Series, Feb. 2004, 106 pages, vol. 24.

Kreuz, T. et al., "Measure Profile Surrogates: A Method to Validate the Performance of Epileptic Seizure Prediction Algorithms," Jun. 15, 2004, Physical Review, pp. 1-9, vol. 69, No. 061915.

Lachaux, J-P. et al., "Measuring Phase Synchrony in Brain Signals," Human Brain Mapping, 1999, pp. 194-208, vol. 8.

Lai, Y-C. et al., "Inability of Lyapunov Exponents to Predict Epileptic Seizures," Physical Review Letters, Aug. 8, 2003, pp. 1-4, vol. 91, No. 6.

Lai, Y-C. et al., "Controlled Test for Predictive Power of Lyapunov Exponents: Their Inability to Predict Epileptic Seizures," Chaos, Sep. 2004, pp. 630-642, vol. 14, No. 3.

Latka, M. et al., "Wavelet Analysis of Epileptic Spikes," Dec. 22, 2002, pp. 1-6.

Le Van Quyen, M., "Anticipating Epileptic Seizures: From Mathematics to Clinical Applications," C.R. Biologies, 2004, pp. 1-12.

Le Van Quyen, M. et al., "Preictal State Identification by Synchronization Changes in Long-Term Intracranial EEG Recordings," Clinical Neurophysiology, 2005, pp. 559-568, vol. 116.

Le Van Quyen, M. et al., "Nonlinear Analyses of Interictal EEG Map the Brain Interdependences in Human Focal Epilepsy," Physica D, 1999, pp. 250-266, vol. 127, Elsevier.

Le Van Quyen, M. et al., "Anticipating Epileptic Seizures in Real Time by a Non-Linear Analysis of Similarity Between EEG Recordings," NeuroReport, Jul. 13, 1999, pp. 2149-2155, vol. 10, No. 10.

Le Van Quyen, M. et al., "Comparison of Hilbert Transform and Wavelet Methods for the Analysis of Neuronal Synchrony," Journal of Neuroscience Methods, 2001, pp. 83-98, vol. 111, Elsevier.

Le Van Quyen, M. et al., "Authors' Second Reply," Correspondence, The Lancet, Mar. 15, 2003, p. 971, vol. 361.

Lehnertz, K. et al., "The First International Collaborative Workshop on Seizure Prediction: Summary and Data Description," Clinical Neurophysiology, 2005, pp. 493-505, vol. 116, Elsevier.

Lehnertz, K., "Non-Linear Time Series Analysis of Intracranial EEG Recordings in Patients with Epilepsy—An Overview," International Journal of Psychophysiology, 1999, pp. 45-52, vol. 34, Elsevier.

Lehnertz, K. et al., "Nonlinear EEG Analysis in Epilepsy: Its Possible Use for Interictal Focus Localization, Seizure Anticipation, and Prevention," Journal of Clinical Neurophysiology, 2001, pp. 209-222, vol. 18, No. 3.

Lehnertz, K. et al., "Seizure Prediction by Nonlinear EEG Analysis," IEEE Engineering in Medicine and Biology Magazine, Jan./Feb. 2003, pp. 57-63.

Lemos, M.S. et al., "The Weighted Average Reference Montage," Electroencephalography and Clinical Neurophysiology, 1991, pp. 361-370, vol. 79, Elsevier Scientific Publishers Ireland, Ltd.

Li, D. et al., "Non-Linear, Non-Invasive Method for Seizure Anticipation in Focal Epilepsy," Mathematical Biosciences, 2003, pp. 63-77, vol. 186, Elsevier.

Li, D. et al, "Linear and Nonlinear Measures and Seizure Anticipation in Temporal Lobe Epilepsy," Journal of Computational Neuroscience, 2003, pp. 335-345, vol. 15, Kluwer Academic Publishers, Netherlands.

Li, X. et al, "Fractal Spectral Analysis of Pre-Epileptic Seizures in Terms of Criticality," Journal of Neural Engineering, Mar. 8, 2005, pp. 11-16, vol. 2.

Litt, B. et al., "Prediction of Epileptic Seizures," Neurology, The Lancet, May 2002, pp. 22-30, vol. 1, No. 1.

Litt, B. et al., "Seizure Prediction and the Preseizure Period," Current Opinion in Neurology, 2002 pp. 173-177, vol. 15.

Maiwald, T. et al., "Comparison of Three Nonlinear Seizure Prediction Methods by Means of the Seizure Prediction Characteristic," Physica D, 2004, pp. 357-368, vol. 194.

Mangasarian, O.L. et al., "Lagrangian Support Vector Machines," Mar. 9, 2006, pp. 1-22.

Martinerie, J. et al., "Epileptic Seizures can be Anticipated by Non-Linear Analysis," Nature Medicine, Oct. 1998, pp. 1173-1176, vol. 4, No. 10.

McSharry, P.E., "Detection of Dynamical Transitions in Biomedical Signals Using Nonlinear Methods," in Knowledge-Based Intelligent Information and Engineering Systems, 2004, pp. 483-490.

McSharry, P.E. et al., "Linear and Non-Linear Methods for Automatic Seizure Detection in Scalp Electro-Encephalogram Recordings," Medical & Biological Engineering & Computing, 2002, pp. 447-461, vol. 40.

McSharry, P.E. et al., "Comparison of Predictability of Epileptic Seizures by a Linear and a Nonlinear Method," IEEE Transactions on Biomedical Engineering, May 2003, pp. 628-633, vol. 50, No. 5.

Meng, L. et al., "Gaussian Mixture Models of EcoG Signal Features for Improved Detection of Epileptic Seizures," Medical Engineering & Physics, 2004, pp. 379-393, vol. 26, Elsevier.

Mizuno-Matsumoto, Y. et al., "Wavelet-Crosscorrelation Analysis Can Help Predict Whether Bursts of Pulse Stimulation Will Terminate Afterdischarges," Clinical Neurophysiology, 2002, pp. 33-42, No. 113, Elsevier.

Mormann, F. et al., "Automated Detection of a Preseizure State Based on a Decrease in Synchronization in Intracranial Electroencephalogram Recordings from Epilepsy Patients," Physical Review, Feb. 26, 2003, vol. 67, No. 021912, The American Physical Society.

Mormann, F. et al., "Epileptic Seizures are Preceded by a Decrease in Synchronization," Epilepsy Research, 2003, pp. 173-185, vol. 53.

Mormann, F. et al., "On the Predictability of Epileptic Seizures," Clinical Neurophysiology, 2005, pp. 569-587, vol. 116, Elsevier.

Mormann, F. et al., "Seizure Anticipation: From Algorithms to Clinical Pratice," Current Opinion in Neurology, 2006, pp. 187-193, vol. 19, Lippincott Williams & Wilkins.

Mormann, F. et al., "Seizure Prediction: The Long and Winding Road," Brain, 2007, pp. 314-333, vol. 130.

Mormann, F. et al., "Mean Phase Coherence as a Measure for Phase Synchronization and its Application to the EEG of Epilepsy Patients," Physica D, 2000, pp. 358-369, vol. 144, Elsevier.

Navarro, V. et al., "Seizure Anticipation in Human Neocortical Partial Epilepsy," Brain, 2002, pp. 640-655, vol. 125.

Navarro, V. et al., "Seizure Anticipation: Do Mathematical Measures Correlate with Video-EEG Evaluation?" Epilepsia, 2005, pp. 385-396, vol. 46, No. 3.

Niederhauser, J.J. et al., "Detection of Seizure Precursors from Depth-EEG Using a Sign Periodogram Transform," IEEE Transactions on Biomedical Engineering, Apr. 2003, pp. 449-458, vol. 51, No. 4.

Nigam, V. et al., "A Neural-Network-Based Detection of Epilepsy," Neurological Research, Jan. 2004, pp. 55-60, vol. 26.

Osorio, I. et al., "Real-Time Automated Detection and Quantitative Analysis of Seizures and Short-Term Prediction of Clinical Onset," Epilepsia, 1998, pp. 615-627, vol. 39, No. 6.

Osorio, I. et al., "Performance Reassessment of a Real-Time Seizure-Detection Algorithm on Long ECoG Series," Epilepsia, 2002, pp. 1522-1535, vol. 43, No. 12.

Osorio, I. et al., "Automated Seizure Abatement in Humans Using Electrical Stimulation," Ann. Neurol., 2005, pp. 258-268, vol. 57, Wiley-Liss, Inc.

Ossadtchi, A. et al., "Hidden Markov Modelling of Spike Propagation from Interictal MEG Data," Physics in Medicine and Biology, Jul. 6, 2005, pp. 3447-3469, vol. 50, Institute of Physis Publishing.

Pflieger, M.E. et al., "A Noninvasive Method for Analysis of Epileptogenic Brain Connectivity," Presented at the American Epilepsy Society 2004 Annual Meeting, New Orleans, LA, Dec. 6, 2004, pp. 1-12.

Pittman, V., "Flexible Drug Dosing Produces Less Side-Effects in People with Epilepsy," Medical News Today Article, Dec. 29, 2005, [online] [Retrieved on Apr. 17, 2006] Retrieved from the Internet<URL:http://www.medicalnewstoday.com/printerfriendlynews.php?newsid=35478>.

Platt, J.C., "Using Analytic QP and Sparseness to Speed Training of Support Vector Machines," To Appear in Advances in Neural Information Processing Systems, M.S. Kearns et al. (Eds.), 1999, pp. 1-8, MIT Press.

Platt, J.C. et al., "Large Margin DAGs for Multiclass Classification," MIT Press, 2000, S.A. Solla et al. (Eds.), pp. 547-553.

Protopopescu, V.A. et al., "Epileptic Event Forewarning from Scalp EEG," Journal of Clinical Neurphysiology, 2001, pp. 223-245, vol. 18, No. 3., Lippincott Williams & Wilkins, Inc.

Rahimi, A. et al., "On the Effectiveness of Aluminum Foil Helmets: An Empirical Study," Feb. 17, 2005, [online] [Retrieved on Dec. 13, 2005] Retrieved from the Internet<URL:http://people.csail.mit.edu/rahimi/helmet/>.

Remington's, 18th Edition, A.R. Gennaro (Ed.), Pharmaceutical Sciences, 1990, 5 pages, Mack Publishing Company.

Robinson, P.A. et al., "Steady States and Global Dynamics of Electrical Activity in the Cerebral Cortex," Phys. Rev. E, Mar. 5, 1998, 13 pages, vol. 58, Issue 3.

Rudrauf, D. et al., "Frequencey Flows and the Time-Frequency Dynamics of Multivariate Phase Synchronization in Brain Signals," NeuroImage, 2005, pp. 1-19.

Saab, M.E. et al., "A System to Detect the Onset of Epileptic Seizures in Scalp EEG," Clinical Neurophysiology, 2005, pp. 427-442, vol. 116, Elsevier.

Sackellares, J.C. et al., "Epilepsy—When Chaos Fails," in Chaos in the Brain? K. Lehnertz et al. (Eds.), Jan. 3, 2000, pp. 1-22.

Sackellares, J.C. et al., "Measurement of Chaos to Localize Seizure Onset," Epilepsia, Sep./Oct. 1989, p. 663, vol. 30, No. 5.

Sackellares, J.C. et al., "Computer-Assisted Seizure Detection Based on Quantitative Dynamical Measures," Electroencephalography and Clinical Neurophysiology, 1995, p. 18P, vol. 95, No. 2.

Sackellares, J.C. et al., "Dynamical Studies of Human Hippocampus in Limbic Epilepsy," Neurology, Apr. 1995, p. A404-A405, vol. 45, Suppl. 4.

Sackellares, J.C. et al., "Relationship Between Hippocampal Atrophy and Dynamical Measures of EEG in Depth Electrode Recordings," Electroencephalography and Clinical Neurophysiology, Jan. 1997, vol. 102, No. 1.

Sackellares, J.C. et al., "Epileptic Seizures as Neural Resting Mechanisms," Epilepsia, Abstracts from the 22nd International Epilepsy Congress, Dublin Ireland, Jun. 29-Jul. 4, 1997, 1 page, vol. 38, Suppl. 3, Lippincott-Raven Publishers.

Sackellares, J.C. et al., "Predictability Analysis for an Automated Seizure Prediction Algorithm," Journal of Clinical Neurophysiology, Dec. 2006, pp. 509-520, vol. 23, No. 6.

Salant, Y. "Prediction of Epileptic Seizures from Two-Channel EEG," Medical & Biological Engineering & Computing, Sep. 1998, pp. 549-556, vol. 36.

Schelter, B. et al., "Testing Statistical Significance of Multivariate Time Series Analysis Techniques for Epileptic Seizure Prediction," Chaos, 2006, pp. 1-10, vol. 16, No. 013108.

Schelter, B. et al., "Testing for Directed Influences Among Neural Signals Using Partial Directed Coherence," Journal of Neuroscience Methods, 2005, pp. 1-10, Elsevier.

Schindler, K. et al., "EEG Analysis with Simulated Neuronal Cell Models Helps to Detect Pre-Seizure Changes," Clinical Neurophysiology, 2002, pp. 604-614, vol. 113, Elsevier.

Schwartzkroin, P.A., "Progres in Epilepsy Research—Origins of the Epileptic State," Epilepsia, 1997, pp. 853-858, vol. 38, No. 8, Lippincott-Raven Publishers.

Sheridan, T.B., "Humans and Automation—System Design and Research Issues," HFES Issues in Human Factors and Ergomonics Series, 2002, 6 pages, vol. 3, John Wiley & Sons, Inc.

Shoeb, A. et al., "Patient-Specific Seizure Detection," MIT Computer Science and Artificial Intelligence Laboratory, Epilepsy & Behavior, 2004, pp. 193-194.

Staba, R.J. et al., "Quantitative Analysis of High-Frequency Oscillations (80-500 Hz) Recorded in Human Epileptic Hippocampus and Entorhinal Cortex," J. Neurophysiology, 2002, pp. 1743-1752, vol. 88.

Stefanski, A. et al., "Using Chaos Synchronization to Estimate the Largest Lyapunov Exponent of Nonsmooth Systems," Discrete Dynamics in Nature and Society, 2000, pp. 207-215, vol. 4.

Subasi, A. et al., "Classification of EEG Signals Using Neural Network and Logistic Regression," Computer Methods and Programs in Biomedicine, 2005, pp. 87-99, vol. 78, Elsevier.

Szoka, Jr., F. et al., "Procedure for Preparation of Liposomes with Large Internal Aqueous Space and High Capture by Reverse-Phase Evaporation," Proc. Natl. Acad. Sci., Sep. 1978, pp. 4194-4198, vol. 75, No. 9.

Tass, P. et al., "Detection of $n{:}m$ Phase Locking from Noisy Data: Application to Magnetoencephalography," Physical Review Letters, Oct. 12, 1998, pp. 3291-3294, vol. 81, No. 15.

Terry, J.R. et al., "An Improved Algorithm for the Detection of Dynamical Interdependence in Bivariate Time-Series," Biol. Cybern., 2003, pp. 129-136, vol. 88.

Tetzlaff, R. et al., "Cellular Neural Networks (CNN) with Linear Weight Functions for a Prediction of Epileptic Seizures," International Jounal of Neural Systems, 2003, pp. 489-498, vol. 13, No. 6, World Scientific Publishing Company.

Theiler, J. et al., "Testing for Nonlinearity in Time Series: the Method of Surrogate Data," Physica D, 1992, pp. 77-94, vol. 58.

Tsakalis, K.S., "Prediction and Control of Epileptic Seizures: Coupled Oscillator Models," Arizona State University, no date, 53 pages.

Tsakalis, K.S., "Prediction and Control of Epileptic Seizures: Coupled Oscillator Models," Part 1, Arizona State University, no date, 25 pages.

Tsakalis, K.S., "Prediction and Control of Epileptic Seizures: Coupled Oscillator Models," Part 2, Arizona State University, no date, 28 pages.

Van Drongelen, W. et al., "Seizure Anticipation in Pediatric Epilepsy: Use of Kolmogorov Entropy," Pediatric Neurology, 2003, pp. 207-213, vol. 29, No. 3.

Van Putten, M.J.A.M., "Nearest Neighbor Phase Synchronization as a Measure to Detect Seizure Activity from Scalp EEG Recordings," Journal of Clinical Neurophysiology, 2003, pp. 320-325, vol. 20, No. 5.

Venugopal, R. et al., "A New Approach Towards Predictability of Epileptic Seizures: KLT Dimension," ISA, 2003, Paper #2003-022, pp. 123-128.

Vonck, K. et al., "Long-Term Amygdalohippocampal Stimulation for Refractory Temporal Lobe Epilepsy," Annals of Neurolology, Nov. 2002, pp. 556-565, vol. 52, No. 5.

Vonck, K. et al., "Neurostimulation for Refractory Epilepsy," Acta Neurol. Belg., 2003, pp. 213-217, vol. 103.

Vonck, K. et al., "Long-Term Deep Brain Stimulation for Refractory Temporal Lobe Epilepsy," Epilepsia, 2005, pp. 98-99, vol. 46, Suppl. 5.

Weiss, P., "Seizure Prelude Found by Chaos Calculation," ScienceNewsOnline, May 23, 1998, [online] [Retrieved on Oct. 18, 2005] Retrieved from the Internet<URL:http://www.sciencenews.org/pages/sn_arc98/5_23_98/fob2.htm>.

Wells, R.B., "Spatio-Temporal Binding and Dynamic Cortical Organization: Research Issues," Mar. 2005, pp. 1-68.

Widman, G. et al., "Reduced Signal Complexity of Intracellular Recordings: A Precursor for Epileptiform Activity?" Brain Research, 1999, pp. 156-163, vol. 836, Elsevier.

Winterhalder, M. et al., "The Seizure Prediction Characteristic: A General Framework to Assess and Compare Seizure Prediction Methods," Epilepsy & Behavior, 2003, pp. 318-325, vol. 4.

Winterhalder, M. et al., "Sensitivity and Specificity of Coherence and Phase Synchronization Analysis," Dec. 28, 2004, pp. 1-21.

Wong, S. et al., "A Stochastic Framework for Evaluationg Seizure Prediction Algorithms Using Hidden Markov Models," J. Neurophysiol., Oct. 4, 2006, pp. 2525-2532, vol. 97.

Yang, H-J. et al., "Relation Between Responsiveness to Neurotransmitters and Complexity of Epileptiform Activity in Rat Hippocampal CA1 Neurons," Epilepsia, 2002, pp. 1330-1336, vol. 43, No. 11.

Yang, K. et al., "*CleVer*: A Feature Subset Selection Technique for Multivariate Time Series," PAKDD 2005, LNAI 3518, T.B. Ho et al. (Eds.), 2005, pp. 516-522, Springer-Verlag.

Yang, K. et al., "A Supervised Feature Subset Selection Technique for Multivariate Time Series," Proceedings of the Workshop on Feature Selection for Data Mining, 2005 SIAM International Conference on Data Mining, Apr. 23, 2005, Newport Beach, CA, 10 pages.

Yang, M.C.K. et al., "Testing Whether a Prediction Scheme is Better Than Guess," Chapter 14, Quantitative Neuroscience, 2004, pp. 251-262, Springer.

Yatsenko, V. et al., "Geometric Models, Fiber Bundles and Biomedical Applications," Proceedings of Institute of Mathematics of NAS of Ukraine, 2004, pp. 1518-1525, vol. 50, Part 3.

Zhaveri, H.P. et al., "Time-Frequency Analyses of Non-Stationary Brain Signals," Electroencephalography & Clinical Neurophysiology, Aug. 1991, pp. 28P-29P, vol. 79, No. 2.

Zhang, X. et al., "High-Resolution EEG: Cortical Potential Imaging of Interictal Spikes," Clinical Neurophysiology, 2003, pp. 1963-1973, vol. 114.

Avanzini, G., "Is Tolerance to Antiepileptic Drugs Clinically Relevant?" Epilepsia, 2006, pp. 1285-1287, vol. 47, No. 8, Blackwell Publishing, Inc.

Curry, W.J. et al., "New Antiepileptic Drugs: Gabapentin, Lamotrigine, Felbamate, Topiramate and Fosphenytoin," American Family Physician, Feb. 1, 1998, 9 pages, vol. 57, No. 3.

Laroche, S.M. et al., "The New Antiepileptic Drugs," Scientific Review, JAMA, Feb. 4, 2004, pp. 605-614, vol. 291, No. 5.

Ochoa, J.G. et al., "Antiepileptic Drugs: An Overview," eMedicine.com, WebMD, updated Sep. 26, 2006, 26 pages.

* cited by examiner

REDUCTION OF CLASSIFICATION ERROR RATES AND MONITORING SYSTEM USING AN ARTIFICIAL CLASS

CROSS REFERENCE TO RELATED APPLICATIONS

The present application claims priority to commonly owned U.S. Provisional Patent Application 60/902,580, filed Feb. 21, 2007, entitled "Methods and Systems for Characterizing and Generating a Patient-Specific Seizure Prediction System," by Snyder et al., the complete disclosure of which is incorporated herein by reference."

BACKGROUND

A variety of systems are used to measure signals and to process and analyze the signals and provide indications of potential or actual conditions that may be advantageous or disadvantageous. When a potential or actual condition is detected, an alert may be provided and/or an action undertaken.

Such systems may use a classification subsystem to analyze the sampled signals and make a determination regarding characteristics of the signals. Classifiers are broadly applicable to data analysis in a wide array of fields such as, for example, medicine (as in the analysis of physiological signals, medical image analysis, clinical trial analysis), computer vision (as in optical character recognition, face recognition), data mining (as in retail analysis), and communications (as in error detection and correction systems, speech recognition, spam filtering). Classification systems generally accept values, which may or may not be numerical, related to some features or characteristics of a situation and produce as an output some label related to the features or characteristics. For example, a classifier might take as input details about a subject's salary, age, assets, marital status, outstanding debt, and the like and classify the subject as either an acceptable or unacceptable credit risk. As another example, a medical device system might measure electrical signals representative of brain activity and characterize the signals as indicative of an inter-ictal (not seizure) condition or a pre-ictal (pre-seizure) condition.

Classification errors can be troublesome. In the case of medical device systems, classification errors can lead to false positive or false negative indications. Both types of classification errors can be significant and may lead to unnecessary intervention, failure to intervene appropriately, and/or erroneous outputs to the subject, which over time, could reduce the value of the medical device system to the user.

SUMMARY

Systems and methods of reducing the error rate for classifiers and for identifying and indicating uncertainty in classifier outputs are disclosed herein. Embodiments are described below that employ the disclosed systems and methods to improve the accuracy of seizure prediction and detection systems. The embodiments may also be configured to provide indications to a user in cases of uncertain or unreliable classification.

A classifier examines a feature vector, having one or more components, and attempts to apply a class label to it. The components of the feature vector are commonly numerical values, but need not be. Classifiers are first trained by exposing them to a set of data, such as a set of training feature vectors. The training feature vectors may each be associated with a predefined class label, as in supervised learning, or the feature vectors may not have associated predefined class labels, as in unsupervised learning. In embodiments using unsupervised learning, a set of classes is constructed to fit the training feature vectors. For example, data clustering, such as K-means, possibly combined with Bayesian inference, may be used to construct a classification based on clusters identified in the training feature vectors. In order to tune a classifier to the particular user, the classifier parameters may be adjusted so as to optimize some performance metric such as, for example, minimizing a classification error rate.

However, it may not be possible in some circumstances to identify, a priori, all possible classes or to provide training feature vectors representative of all possible classes. Conventional classification strategies are subject to the limitations of the data that they have been configured to recognize. Classifiers can make erroneous decisions when exposed to data from an unanticipated class, or data containing noise or other artifacts. If a conventional classifier is presented with a feature vector that is representative of an unknown, unidentified class, a classification error results because the classifier is forced to apply one of the known class labels to the input feature vector. This occurs even if the input feature vector is atypical of the applied classification.

In some embodiments of seizure prediction systems, physiological signals, generally including electrical signals indicative of brain activity, are measured and a feature vector representative of one or more aspects of the measured signals is constructed. A classifier is applied to the feature vector and a corresponding neurological condition is associated with the feature vector. In some embodiment, the possible neurological conditions include ictal, pre-ictal, pro-ictal, inter-ictal, contra-ictal, and post-ictal. The consequences of a classification error may include a failure to suitably warn a monitored subject and/or to appropriately intervene.

An artificial class (sometimes referred to herein as an "other" class), which may be thought of as representing a potentially unknown, unidentified class, is introduced. The addition of the artificial class explicitly accounts for the occurrence of unanticipated data measurements that may result from different sources, e.g., uncharacterized brain states, system noise, measurement artifacts introduced by non-neural signal sources, and so forth. The artificial class may reduce false positive rates by ensuring that when a class label is assigned, the feature vector being classified is not atypical of that class. Incorporation of the artificial class into a classifier may reduce the error rate of the classifier, improve therapy, and/or improve the types of outputs provided to the subject, as described more fully below. Various embodiments and techniques for constructing the artificial class are described below.

Embodiments of seizure prediction, detection, or monitoring systems having classifiers embodying an artificial class are described herein. An improved user interface is disclosed wherein a classification resulting in the artificial class is used to provide a subject with an indication of uncertainty or unreliability in a predicted result. Actions may be indicated in response to a classification resulting in the artificial class. In the case of repeated indications related to the artificial class, retraining or reconfiguration of a seizure prediction and detection system may be indicated.

For a further understanding of the nature and advantages of the present invention, reference should be made to the following description taken in conjunction with the accompanying drawings.

DETAILED DESCRIPTION

Figure 1:
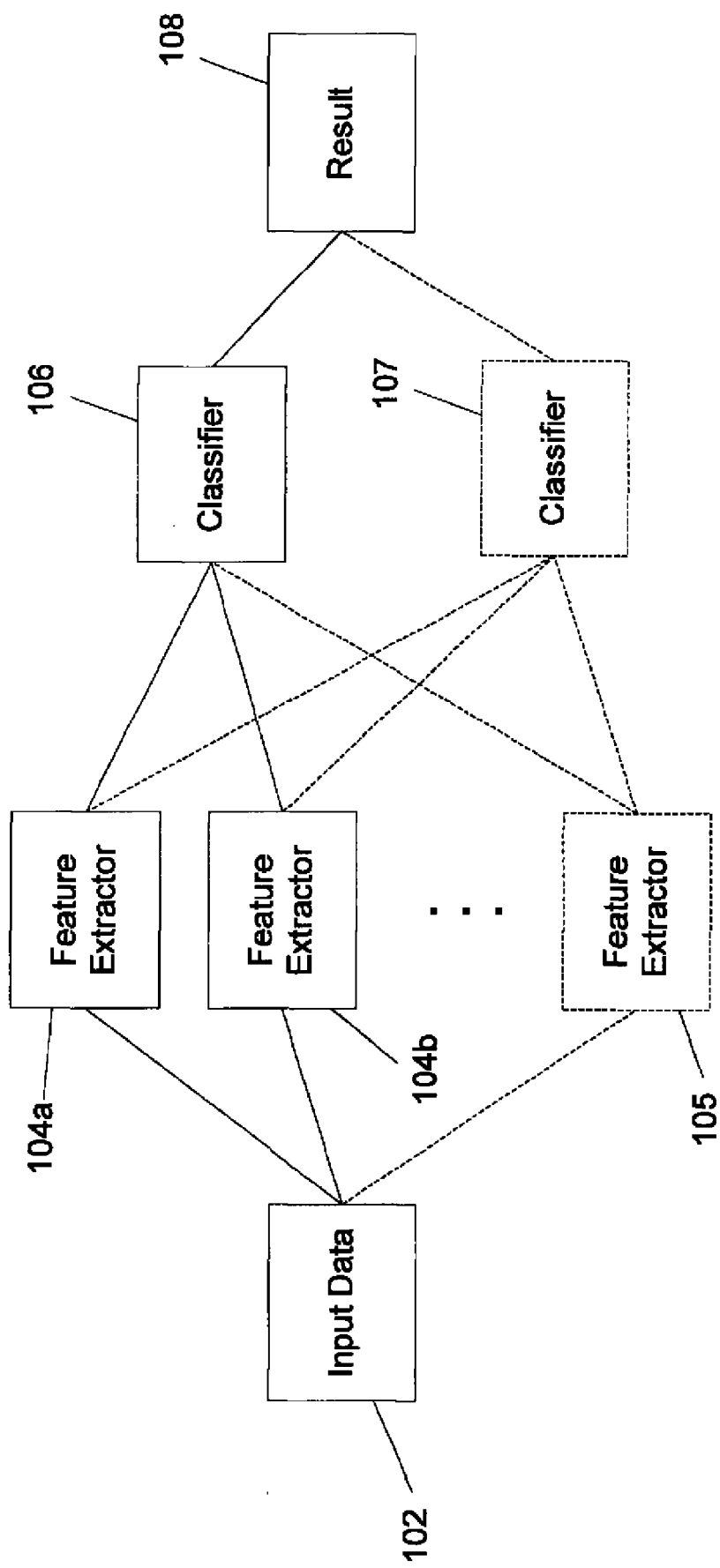
FIG. 1 is a block diagram illustrating aspects of feature extractors and classifiers.

Certain specific details are set forth in the following description and figures to provide an understanding of various embodiments of the invention. Certain well-known details, associated electronics and medical devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

As described in the background, a variety of medical device systems are used to measure physiological signals from a subject and to process those signals. Although some of the discussion below focuses on measuring EEG signals of subjects and subject populations for the detection and prediction of epileptic seizures, it should be appreciated that the invention is not limited to measuring EEG signals or to predicting epileptic seizures. For example, the invention could also be used in systems that measure one or more of a blood pressure, blood oxygenation from pulse oximetry measurements, temperature of the brain or other portions of the subject, blood flow measurements, ECG/EKG, heart rate signals, respiratory signals, chemical concentrations of neurotransmitters, chemical concentrations of medications, pH in the blood, or other physiological or biochemical parameters of a subject.

Furthermore, aspects of the invention may be useful for monitoring and assisting in the treatments for a variety of conditions such as sleep apnea and other sleep disorders, migraine headaches, depression, Alzheimer's, Parkinson's Disease, dementia, attention deficit disorder, stroke, eating disorders, addiction, other neurological or psychiatric disorders, cardiac disease, diabetes, cancer, or the like.

Using epilepsy as an illustrative example, epilepsy is a disorder of the brain characterized by chronic, recurring seizures and affects an estimated 50 million people worldwide. Seizures are a result of uncontrolled discharges of electrical activity in the brain. A seizure typically manifests itself as sudden involuntary, disruptive, and often destructive sensory, motor, and cognitive phenomena. Epilepsy is usually treated, though not cured, with medication. Surgery may be indicated in cases in which seizure focus is identifiable, and the seizure focus is not located in the eloquent cortex.

A single seizure most often does not cause significant morbidity or mortality, but severe or recurring neurological conditions can result in major medical, social, and economic consequences. Epilepsy is more often diagnosed in children and young adults. People with uncontrolled epilepsy are often significantly limited in their ability to work in many industries and may not be able to legally drive an automobile.

The cause of epilepsy is often uncertain. Symptomatic epilepsies arise due to some structural or metabolic abnormality of the brain and may result from a wide variety of causes including genetic conditions, stroke, head trauma, complications during pregnancy or birth, infections such as bacterial or viral encephalitis, or parasites. Idiopathic epilepsies are those for which no other condition has been implicated as a cause and are often genetic and generalized. In the majority of cases, the cause of a subject's epilepsy is unknown.

One of the most disabling aspects of neurological disorders such as epilepsy is the seeming unpredictability of neurological conditions such as seizures. Mechanisms underlying the generation of seizures are thought to operate over a period of seconds to minutes before the clinical onset of a seizure. Typically, electrographic manifestations of a neurological condition are detectable some time before clinical manifestations occur. Most work in the quantitative analysis of neurological conditions has been aimed at detecting these electrographic manifestations. For example, NeuroPace, Inc. has been developing systems to detect the electrographic onset of a neurological condition so that some action, such as direct electrical stimulation of certain brain structures, may be taken in an attempt to preempt the clinical onset of a neurological condition. However, the detection of the electrographic onset of a neurological condition may not come far enough in advance of the clinical onset for electrical stimulation or other therapies, such as the administration of anticonvulsant drugs, to be effective in preventing the clinical onset. Additionally, seizure activity may already be causing harm to the brain before the clinical onset of the seizure.

It is desirable to be able to predict neurological conditions well before their electrographic onset. Embodiments of predictive systems generally comprise a collection of detectors for acquiring data from a subject and an analysis system for processing the data to measure a subject's susceptibility or propensity for a seizure. Predictive analysis systems are routinely considered to be comprised of arrangements of feature extractors and classifiers. Feature extractors are used to quantify or characterize certain aspects of the measured input signals. Classifiers are then used to combine the results obtained from the feature extractors into an overall answer or result. Systems may be designed to detect different types of conditions that may be reflective of neural condition. These could include, but are not limited, to systems designed to detect if the subject's neural condition is indicative of an increased susceptibility or propensity for a neurological condition or systems designed to detect deviation from a normal condition. As can be appreciated, for other neurological or non-neurological disorders, the classification of the subject's condition will be based on systems, feature extractors and classifiers that are deemed to be relevant to the particular disorder.

FIG. 1 depicts an example of the overall structure of a system for estimating a propensity for the onset of a neurological condition such as, for example, an epileptic seizure. The input data 102 may comprise representations of physiological signals obtained from monitoring a subject. The input data may be in the form of analog signal data or digital signal data that has been converted by way of an analog to digital converter (not shown). The signals may also be amplified, preprocessed, and/or conditioned to filter out spurious signals or noise. For purposes of simplicity the input data of all of the preceding forms is referred to herein as input data 102.

The input data 102 from the selected physiological signals is supplied to one or more feature extractors 104a, 104b, 105. A feature extractor 104a, 104b, 105 may be, for example, a set of computer executable instructions stored on a computer readable medium, or a corresponding instantiated object or process that executes on a computing device. Certain feature extractors may also be implemented as programmable logic or as circuitry. In general, a feature extractor 104a, 104b, 105 can process data 102 and identify some characteristic of the data 102. Such a characteristic of the data is referred to herein as an extracted feature.

Each feature extractor 104a, 104b, 105 may be univariate (operating on a single input data channel), bivariate (operating on two data channels), or multivariate (operating on multiple data channels). Some examples of potentially useful characteristics to extract from signals for use in determining the subject's propensity for a neurological condition, include but are not limited to, bandwidth limited power (alpha band [8-13 Hz], beta band [13-18 Hz], delta band [0.1-4 Hz], theta band [4-8 Hz], low beta band [12-15 Hz], mid-beta band [15-18 Hz], high beta band [18-30 Hz], gamma band [30-48 Hz], high frequency power [>48 Hz], bands with octave or half-octave spacings, wavelets, etc.), second, third and fourth (and higher) statistical moments of the EEG amplitudes or other features, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STLmax, T-index, angular frequency, and entropy), line length calculations, first, second and higher derivatives of amplitude or other features, integrals, combinations thereof, relationships thereof including ratios and differences. Of course, for other neurological conditions, additional or alternative characteristic extractors may be used with the systems described herein.

The extracted characteristics can be supplied to one or more classifiers 106, 107. Like the feature extractors 104a, 104b, 105, each classifier 106, 107 may be, for example, a set of computer executable instructions stored on a computer readable medium or a corresponding instantiated object or process that executes on a computing device. Certain classifiers may also be implemented as programmable logic or as circuitry. In some embodiments, some classifiers may be optionally applied or omitted in various circumstances. For example, when the application of one or more classifiers 106 is sufficient to estimate that a propensity for a neurological condition is sufficiently low, then other classifiers 107 may not be applied to the extracted characteristics. If the classifiers 106 indicate a higher propensity for a neurological condition, then additional classifiers 107 may be applied to the extracted characteristics.

The classifiers 106, 107 analyze one or more of the extracted characteristics and possibly other subject dependent parameters to provide a result 108 that may characterize, for example, a subject's neural condition. A signal may be generated in response to the classification. As examples, and not by way of limitation, a data signal representative of the classification may be generated, or some indicator may serve to communicate information related to the classification to a user. Some examples of classifiers include k-nearest neighbor ("KNN"), linear or non-linear regression, Bayesian, mixture models based on Gaussians or other basis functions, neural networks, and support vector machines ("SVM"). The classifiers 106, 107 may be customized for the individual subject and may be adapted to use only a subset of the characteristics that are most useful for the specific subject. For example, the classifier may detect pre-onset characteristics of a neurological condition or characteristics that indicate being in a contra-ictal condition. Additionally, over time, the classifiers 106, 107 may be further adapted to the subject, based, for example, in part on the result of previous analyses and may reselect extracted characteristics that are used for the specific subject.

As it relates to epilepsy, for example, one implementation of a classification of neural conditions defined by the classifiers 106, 107 may include classes associated with (1) an inter-ictal condition (sometimes referred to as a "normal" condition), (2) a pre-ictal condition and/or pro-ictal (sometimes referred to as an "abnormal" or "high-susceptibility" condition), (3) an ictal condition (sometimes referred to as a "seizure" condition), (4) a post-ictal condition (sometimes referred to as a "post-seizure" condition), and (5) a contra-ictal condition (referred to herein as a "protected" condition). The term "pro-ictal" is used herein to refer to a neurological state or condition characterized by an increased likelihood of transition to an ictal state. A pro-ictal state may transition to either an ictal or inter-ictal state. A pro-ictal state that transitions to an ictal state is also referred to as pre-ictal.

In another embodiment, it may be desirable to have the classifier classify the subject as being in one of two conditions—a pre-ictal condition or inter-ictal condition—which could correspond, respectively, to either an elevated or high propensity for a future seizure or a low propensity for a future seizure. For ease of reference, the Figures are shown having only two known classes. It should be appreciated, however, that the present invention is applicable to classifiers that have any number of classifications.

Figure 2:
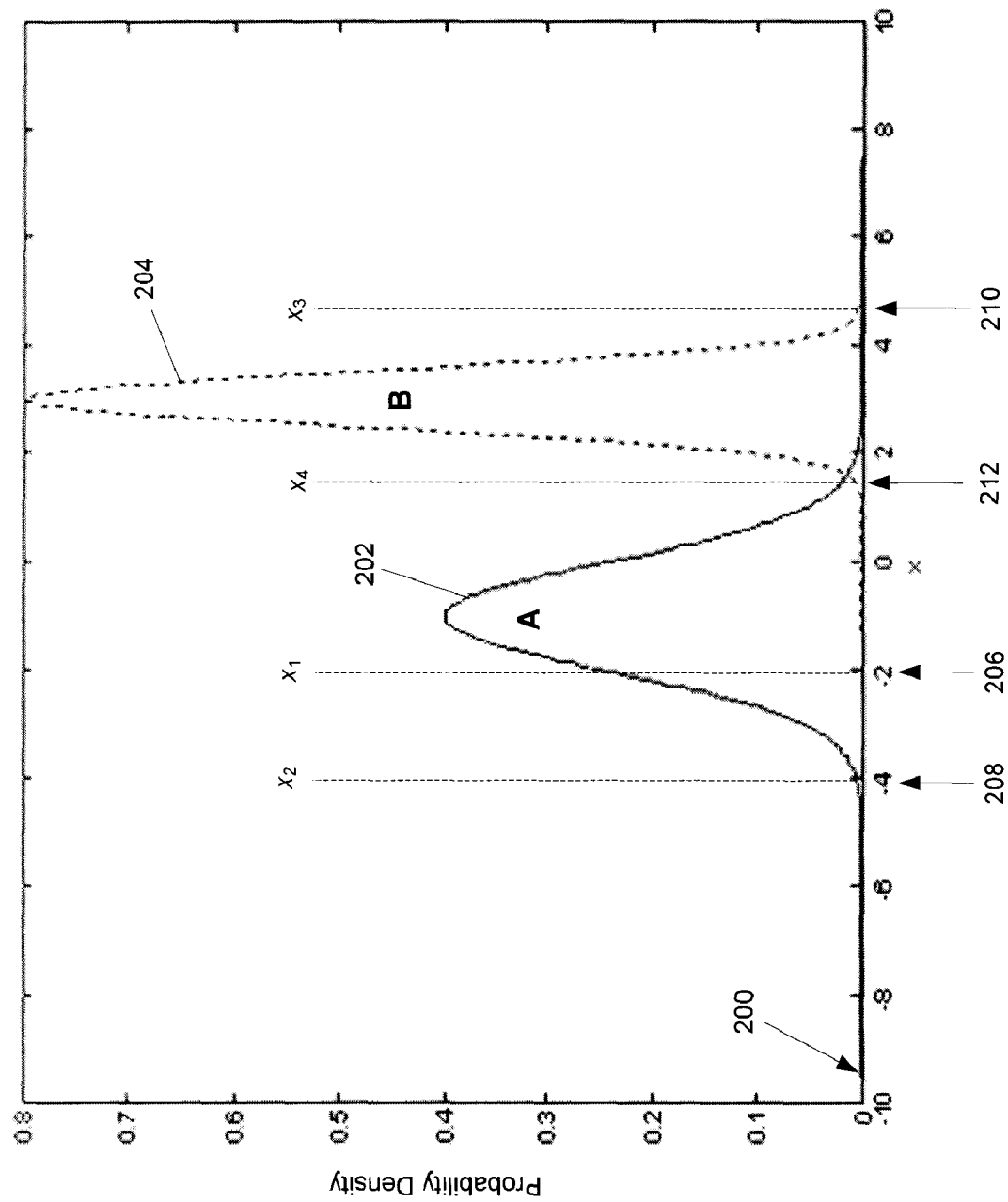
FIG. 2 is a graph of two probability density functions for an example classifier.

FIG. 2 depicts the operation of a conventional classifier that makes use of the probability densities of various classes. The graphs depict the probability density functions ("PDF") of two classes of data. Measurement feature vectors for this hypothetical classifier consist of a single numerical value, x, plotted along a horizontal axis 200. The PDF of a first class, Class A, is plotted as a solid curve 202. The PDF of a second class, Class B, is plotted as a dotted curve 204. A procedure for classifying a measurement is to label the measurement with the class having the greatest PDF value at the measured value x. For example, consider a measurement feature vector with a value of $x_1=-2.0$, indicated by the reference numeral 206. The value of the PDF for Class A 202 at $x_1=-2.0$ is approximately 0.25, while the value of the PDF for Class B 204 is nearly 0.0. Thus, a measurement of $x_1=-2.0$ would be classified as Class A.

Consider an application of the strategy to a measurement of $x_2=-4.0$, indicated by the reference numeral 208. Both PDFs have values near zero, indicating that the value $x_2=-4.0$ is atypical of either class. Nonetheless, the strategy would classify the measurement as Class A because the PDF of Class A is larger. Similarly, a measurement of $x_3=4.5$, indicated by the reference numeral 210, would be classified as Class B even though the measurement is atypical of either class.

Finally, consider a measurement of $x_4=1.5$, indicated by reference numeral 212. The values of the two PDFs are nearly equal at the measurement value. Even though both classes are about equally likely there, the classifier would classify the measurement feature vector of $x_4=1.5$ as Class A because its PDF 202 is slightly higher than the PDF of Class B 204 at the measured value. Because the PDF values are nearly equal, the chance of misclassification is almost 50%, even though we may know a priori that the measurement is associated with one of the two classes.

In some embodiments, the various classes are identified with physical conditions. The classes may be constructed using a training set of data derived from physical measurements and associated with the various classes. For example, in an epilepsy monitoring system, the training set of data may be obtained from measurements of electrical signals indicative of brain activity. Features are extracted from the measured signals and a feature vector with one or more components is determined. An expert reviews the measured signals, and possibly other data associated with the measured signals, and identifies the measured signals and their derived feature vector as associated with a particular class. The training set of feature vectors and their class associations are then used to construct a classifier. In some embodiments, a PDF may be constructed from each class using the feature vectors associated with that class. In some other embodiments, the training set of feature vectors themselves may be used by the classifier, such as, for example, in a KNN classifier.

A conventional classifier, such as for example that described above in relation to FIG. 2, necessarily classifies any given input feature vector in one of the known, predetermined classes. Such a forced response might be acceptable, or even desirable, in some circumstances. For example, if the classifier is incorporated in an automated system that must deterministically execute some course of action in response to a classification, then certainty in classification may be required.

A forced classification choice may not be desirable in some systems. For example, if the classifier of FIG. 2 is associated with a seizure prediction system, and if Class A is associated with an inter-ictal condition and Class B is associated with a pre-ictal or pro-ictal condition, the result of a forced classification could be detrimental. A misclassification into Class A, in such a system, would label a pre-ictal condition as inter-ictal and no warning of a pre-seizure condition would be given. On the other hand, a misclassification into Class B would label a possible inter-ictal condition as pre-ictal or pro-ictal, potentially triggering an unnecessary warning and/or intervention such as, for example, the automatic administration of medication or the direct electrical stimulation of the subject's brain or particular peripheral nerves, such as, for example, the vagus nerve.

Figure 3:
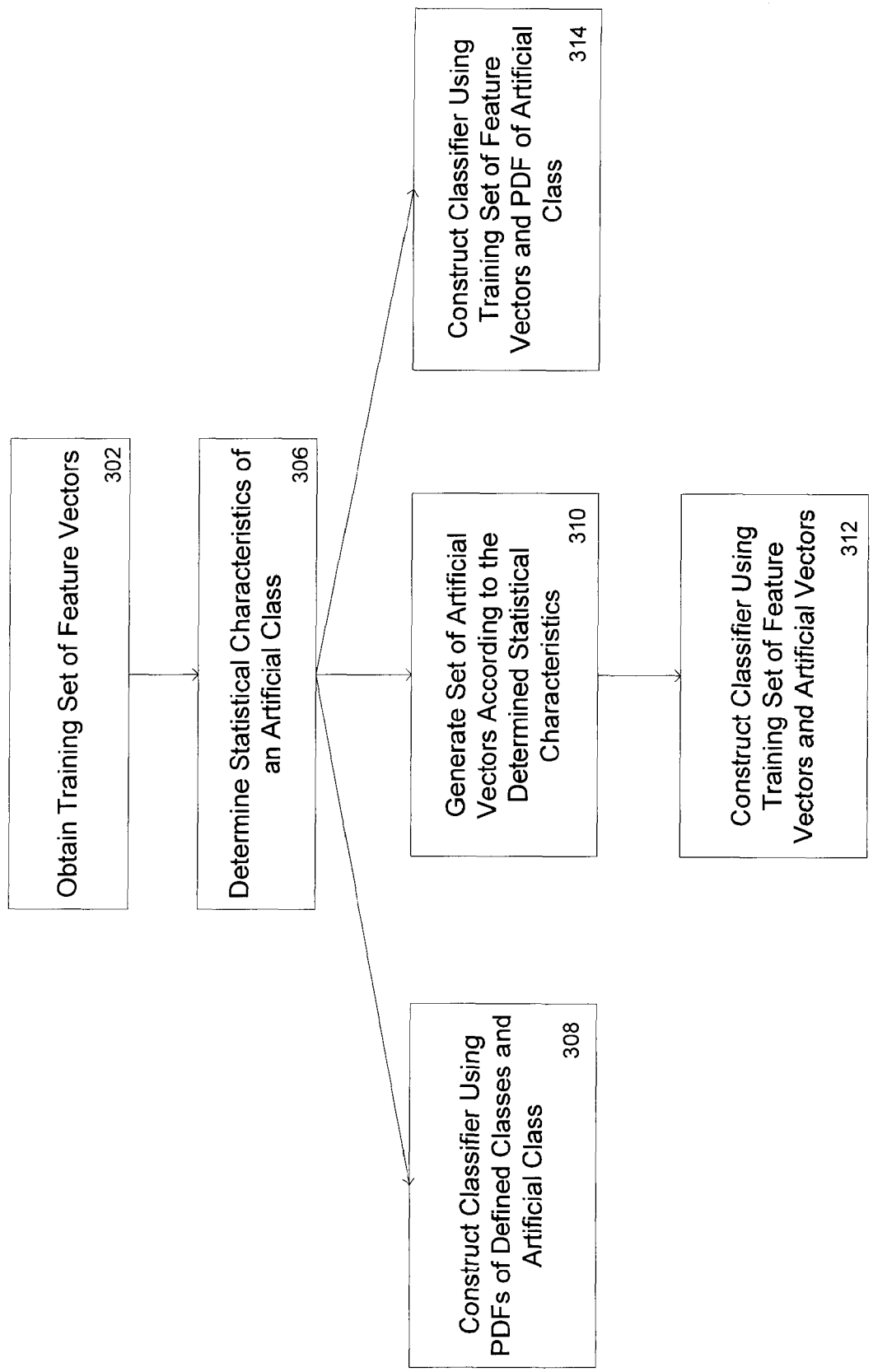
FIG. 3 is a flow chart for some embodiments of ways to construct an artificial class.

FIG. 3 is a flow chart for embodiments of some ways of constructing an artificial class and enhancing the performance of a classifier. A set of training feature vectors is obtained 302. After the statistical characteristics of the training feature vectors are determined, it may be desirable to determine an artificial class 306. For example, statistical characteristics of the entire set of training vectors, regardless of class associations, may be ascertained and used for constructing an artificial class. As another example, a uniform probability distribution may be selected for an artificial class. In general, any PDF may be employed for the artificial class, with various PDFs having different advantages or disadvantages with respect to various performance metrics.

A classifier using closed-form PDFs for the training feature vectors and the artificial class may be constructed 308, such as in examples described below. Alternatively, the determined statistical characteristics for the artificial class can be used to generate a set of artificial vectors associated with the artificial class 310. A classifier is then constructed using both the training set of feature vectors and the artificially generated vectors 312. In yet another alternative embodiment, a classifier may be constructed using the training set of feature vectors and a closed-form PDF for the artificial class 314.

Figure 4:
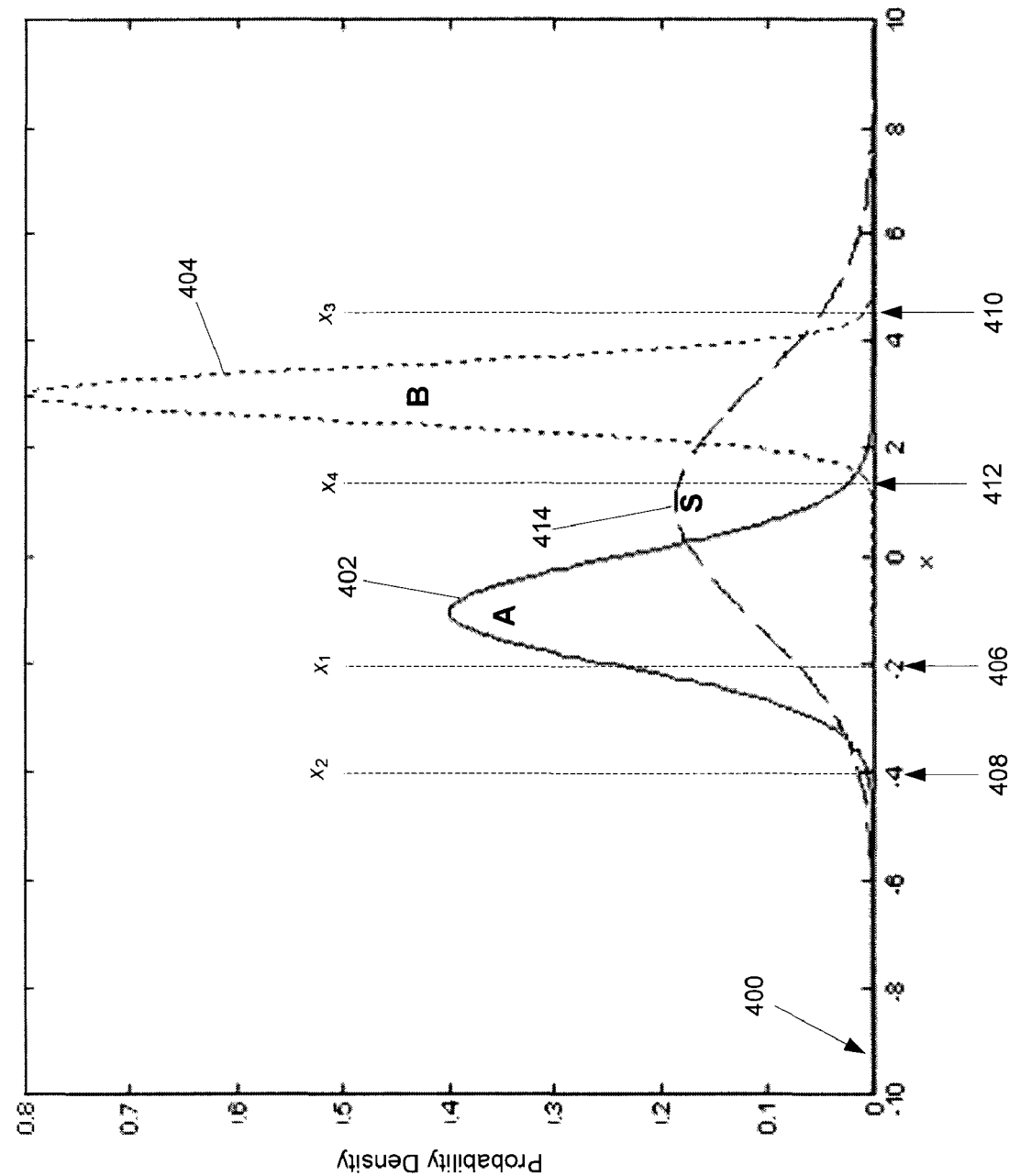
FIG. 4 is a graph of three probability density functions for an embodiment according to the teachings herein.

FIG. 4 depicts an example wherein an artificial class has been added to enhance the classifier of FIG. 2. The graphs of the PDFs of three classes of data described by measurement feature vectors comprising a single numerical value, x, plotted along a horizontal axis 400 are given. The first two, Class A whose PDF is indicated by a solid curve 402 and Class B whose PDF is indicated by a dotted curve 404, are identical to the two classes from the example depicted in FIG. 2 and are referred to as defined or empirical classes. Now, a third, artificial class has been added. It is labeled Class S and its PDF is indicated by a dashed curve 414. The artificial class may be formed using any of the steps 308, 312, 314 shown in FIG. 3. In this example, the artificial Class S has been constructed with a normal distribution having a mean ($\mu$) and standard deviation ($\sigma$) equal to the population statistics for the empirical classes, Class A and Class B, combined:

$$f_x(x) = \frac{1}{\sigma\sqrt{2\pi}} e^{-\frac{(x-\mu)^2}{2\sigma^2}}$$

A classifier using the same strategy of the classifier from the example of FIG. 2 is applied to measurement feature vectors. That is, a measurement feature vector is labeled with the class having the greatest PDF value at the measured value x.

At a value of $x_1=-2.0$, indicated by the reference numeral 406, the value of the PDF of Class A 402, approximately 0.25, is greater than the values for the PDFs of Class S 414, approximately 0.08, and Class B 404, nearly 0.0. Thus, as in the example of FIG. 2, a measurement of $x_1=-2$ would still be classified as Class A.

At values of $x_2=-4.0$, indicated by the reference numeral 408, and $x_3=4.5$, indicated by the reference numeral 410, the value of the PDF of the artificial Class S 414 is greater than the value of the PDF of either empirical class, and so the classifier would label both measurement feature vectors with Class S. The artificial Class S is associated with uncertainty or unreliability in the classification. Thus, measurement feature vectors with $x_2=-4.0$ or $x_3=4.5$, which are atypical of any empirical class, would be identified as "unknown" or "uncertain."

At the value $x_4=1.5$, indicated by reference numeral 412, the value of the PDF of the artificial Class S 414 is greater than the value of the PDF of either empirical class, and so a measurement feature vector with a value of $x_4=1.5$ would be labeled with Class S.

It is expected that the use of an artificial class, such as described above for example, will improve the reliability of a classifier by reducing the frequency of misclassification. The artificial class may capture feature vectors that are either atypical of any of the empirical classes and associate those feature vectors with the artificial class, thereby identifying them as unknown or uncertain with regard to all of the empirical classes. Similarly, the artificial class may capture feature vectors near the boundaries between two classes where the chance of misclassification can be large.

If, for example, the classifier of FIG. 4 is associated with a seizure prediction system, and if Class A is associated with an inter-ictal condition and Class B is associated with a pre-ictal condition, Class S would be associated with an "unknown or uncertain" neurological condition.

The measurement feature vector $x_2$ was assigned the label of Class A, just as in the example of FIG. 2. This is reasonable since $x_2$ is typical of Class A and highly atypical of Class B. In this case, the seizure prediction and detection system would indicate a "normal" condition.

The measurement feature vector $x_2$ was assigned the label of Class S by the enhanced classifier of FIG. 4, whereas $x_2$ was assigned the label of Class A by the classifier of FIG. 2. Thus, the classifier of FIG. 2 would characterize the measurement feature vector $x_2$ as representing an inter-ictal state and the system would indicate a "normal" condition, despite the fact that $x_2$ is highly atypical of an inter-ictal state. A system employing the enhanced classifier of FIG. 4 would instead indicate an "unknown or uncertain" condition, and a user would consequently be warned of the possibility that the measurement feature vector had been particularly susceptible to misclassification. The user, thus alerted, could then take precautions commensurate with that possibility. Such precautions might possibly stop short of the administration of medication or direct electrical stimulation of particular nerves. Instead, for example, the user might be warned to cease activities, such as driving or operating machinery that might be hazardous should a seizure ensue. Similarly, a user would be warned that monitoring results having measurement vectors $x_3$ or $x_4$ result in an unknown or uncertain classification.

In the example of FIG. 4, some statistical qualities, in this case the mean and standard deviation, of the entire population of empirical measurement feature vectors may be used to construct the artificial class. In a sense, this represents the notion that if an undetectable, unrecognized class is present in the data, then any empirical data point could represent a member of the unknown class.

Figure 5:
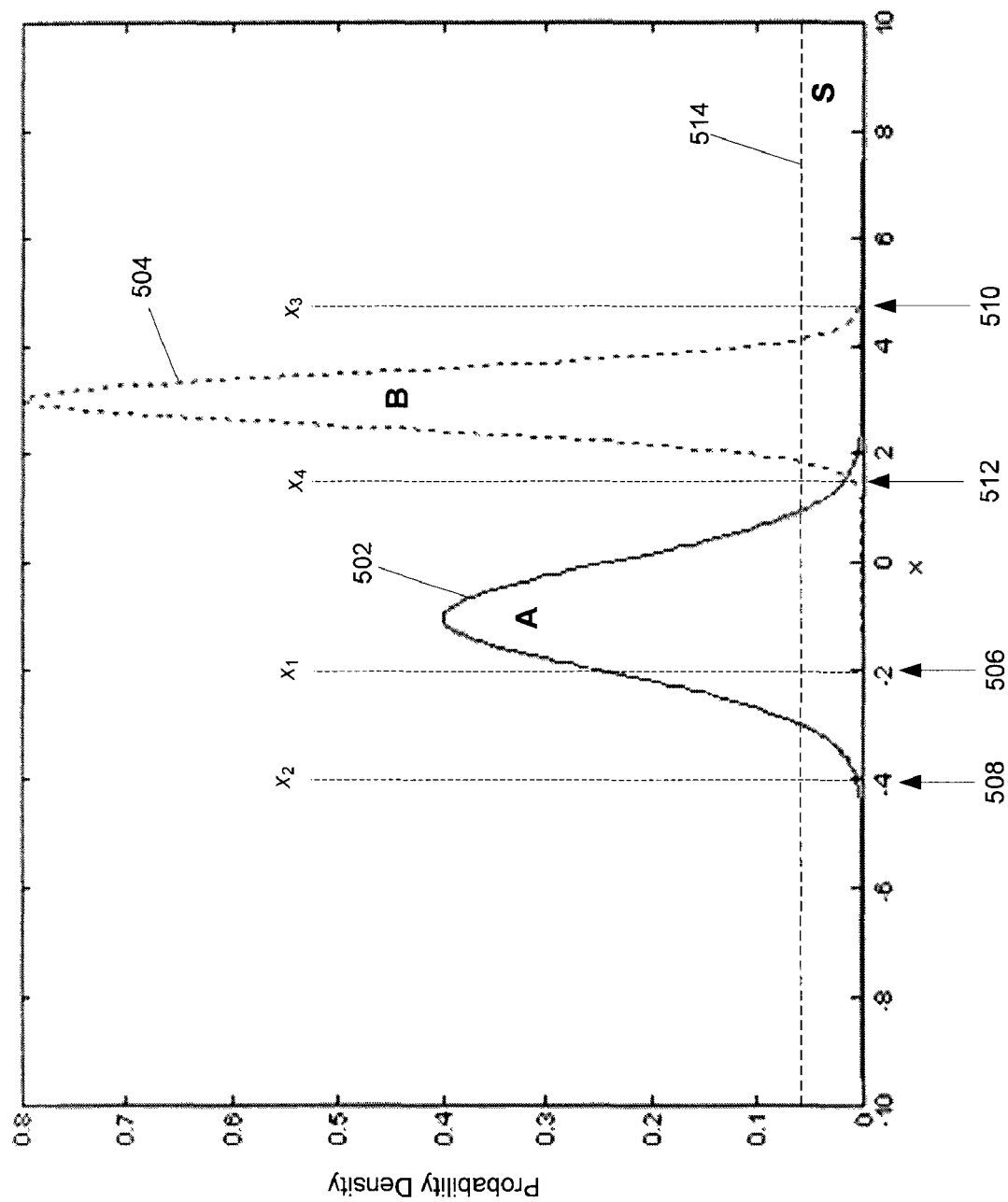
FIG. 5 is a graph of three probability density functions for an embodiment according to the teachings herein.

FIG. 5 depicts an example wherein a uniform distribution is used to create the artificial class. The PDFs of two empirical classes 502 504 and an artificial class 514 are illustrated. The artificial class has been constructed with a uniform distribution, and thus its PDF 514 is constant. Measurement feature vector $x_1$ 506 will be labeled with Class A, while measurement feature vectors $x_2$ 508, $x_3$ 510, and $x_4$ 512 will be labeled with Class S, just as in the example of FIG. 4. The choice of particular probability distribution may affect the boundaries where the classifiers change classes as the measurement feature vector values vary. However, in each case the addition of the artificial class enables the classifier to identify some situations where the classification may be uncertain or unreliable.

The examples given above used a one-dimensional measurement feature vector primarily for simplicity of exposition. The teachings herein are broadly applicable to systems employing multi-dimensional feature vectors. In general, any probability distribution may be used to generate the artificial class. Various PDFs may have different advantages or disadvantages with respect to particular performance metrics. The classification methodology may also be modified in a variety of ways, for example by the consideration of prior probabilities such as used in Bayesian classifier.

In some embodiments, it may be desirable to have only a single identified class associated with the set of training vectors, for example as in a novelty detector. As an example, a training set of vectors may be measured from a subject during a period in which the subject's neurological condition is classified as normal. The introduction of an artificial class will facilitate the classification of subsequently measured feature vectors as "not normal" or "unknown" and may be used to determine deviation from normal.

Additional alternative methods of realizing an artificial class are contemplated by the disclosure herein. For example, an artificial data set, having specified properties, may be generated for use by a classifier. Techniques for generating an artificial data set, for example using random number generation, are known. For example, random numbers with a specified distribution can be generated by inversion of the cumulative distribution function applied to random numbers from a uniform distribution on the unit interval (0,1). The artificial data is then associated with the artificial class and a classifier is trained using both the empirical and artificial data. Other distribution functions suitable for generating an artificial data set include the group of radial basis functions, e.g. Gaussian, multiquadratic, and thin plate spline. Radial basis functions depend on the distance of an observation from a location parameter, where the distance may be geometric (e.g. Euclidean or $L^2$ norm), statistical (e.g. Mahalanobis), or any other suitable distance metric, e.g. $L^1$ norm or other p-norm. Other more general distribution functions may be generated to address specific requirements of a classifier. For example, error rates for a classifier that does not utilize an artificial class can be reduced by characterizing its error rate as a function of position within the feature space. A PDF for an artificial class that is proportional to the characterized error rate can then be constructed. In this manner, observations in error-prone regions of the feature space will be assigned to the artificial class rather than to a defined or empirical class.

As an example, consider a basic k-nearest neighbor ("KNN") classifier. In a KNN classifier, an input feature vector is compared with feature vectors from a training set that have each been identified with an empirical class. The k nearest (according to a distance metric such as, for example the Euclidean or $L^2$ norm) feature vectors from the training set are identified. The value of k is a parameter of the classifier and the best choices for k may depend on the data. Given an input feature vector, its k nearest neighbors from the training set are identified and the input feature vector is associated with the class having the greatest number among those nearest neighbors. Additionally, a probability of class membership may be calculated for each class according to its proportion among the k nearest neighbors. Alternatively, the importance of each of the k-nearest neighbors can be weighted according to its distance from the input feature vector using a radial basis function, so as to assign greater weight to short distances than to long distances.

One technique for enhancing a KNN classifier with the addition of an artificial class is to model an artificial class as a multi-dimensional Gaussian characterized by the overall group statistics of the empirical classes. Such a characterization could use the full covariance matrix for the empirical classes, or could assume that the components of the feature vectors in the artificial class are independent and use only a diagonal covariance matrix. Random artificial feature vectors are generated from the Gaussian model and associated with the artificial class. An input feature vector is classified by identifying its k nearest neighbors among both the training feature vectors and the artificially generated feature vectors. If the artificial class is most numerous among those nearest neighbors, then the input feature vector is associated with the artificial class.

A second technique for enhancing a KNN classifier with the addition of an artificial class does not entail generating artificial feature vectors. Instead, a probability density function $f_0$ for the feature vectors in a training set as a whole is estimated and associated with an artificial class. For example, $f_0$ could be chosen as a multivariate Gaussian density function with covariance matrix, $\Sigma$, equal to that of the complete set of training vectors.

$$f_0(x) = \frac{1}{(2\pi)^{d/2}|\Sigma|^{1/2}} \exp\left[-\frac{1}{2}(x-\mu)^T \Sigma^{-1}(x-\mu)\right]$$

Given an input feature vector, its k nearest neighbors among the training feature vectors are identified. A (possibly multi-dimensional) volume containing those nearest neighbors is estimated. For example, the volume of a hypersphere having a radius R equal to the distance from the input feature vector the $k^{th}$ nearest neighboring vector from the training set could be used.

$$V = \frac{\pi^{d/2} R^d}{\Gamma(d/2 + 1)}$$

where d is the number of dimensions of the feature vectors. One possible variation is to instead use a hypersphere having a radius, R, halfway between the distance to the $k^{th}$ nearest neighboring training vector, $R_k$, and the distance to the $(k+1)^{st}$ nearest neighboring training vectors, $R_{k+1}$, that is, $R=(R_k+R_{k+1})/2$. As another variation, a volume halfway between those of the hypersphere out to the $k^{th}$ nearest and $(k+1)^{st}$ nearest neighbors could be used.

$$V = \frac{\pi^{d/2}}{\Gamma(d/2+1)} \frac{(R_k^d + R_{k+1}^d)}{2}$$

The estimated volume is used together with the probability density associated with the artificial class at the input feature vector to estimate the number of artificial feature vectors that would be expected within the computed volume, $k_0 = f_0 V N_0$ where $N_0$ represents the total number of artificial feature vectors in the feature space. $N_0$ is a parameter that may be selected.

As another example, consider the application of a Bayes classifier to a Gaussian mixture model having n empirical classes $C_1, C_2, \ldots C_n$. Under this model, the posterior probability of membership in a class $C_i$ is:

$$P[C_i|\bar{x}] = \frac{P[C_i]P[\bar{x}|C_i]}{P[\bar{x}]} = \frac{P[C_i]f_x(\bar{x}|C_i)}{\sum_j f_x(\bar{x}|C_j)P[C_j]}$$

where $P[C_i]$ is the prior probability of class $C_i$, commonly taken as the proportion of training vectors in the class $C_i$, and $f_x(\bar{x}|C_i)$ is the PDF as a function of feature vector $\bar{x}$ for class $C_i$. A Bayes classifier would typically classify $\bar{x}$ into the class having the greatest posterior probability. An artificial class can be added, and may, for example, be represented as a Gaussian cluster having location parameter (for example, centroid or mean) equal to the overall mean of the training vectors and a covariance matrix equal to the covariance of the training vectors. The extent of the influence of the artificial class on the classifier can be adjusted by the choice of a prior probability for the artificial class. In general, as the prior probability of the artificial class is increased, a higher proportion of classifications will be made to the artificial class.

Figure 12:
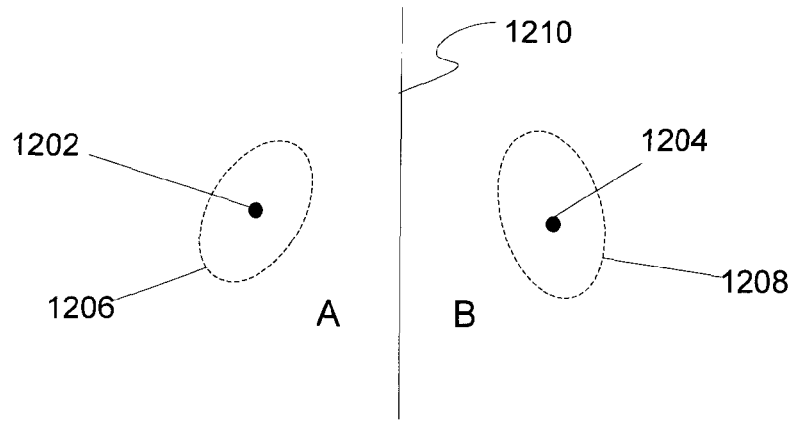
FIG. 12 depicts an example having two-dimensional feature vectors classified into two classes, A and B having Gaussian distributions.
Figure 13:
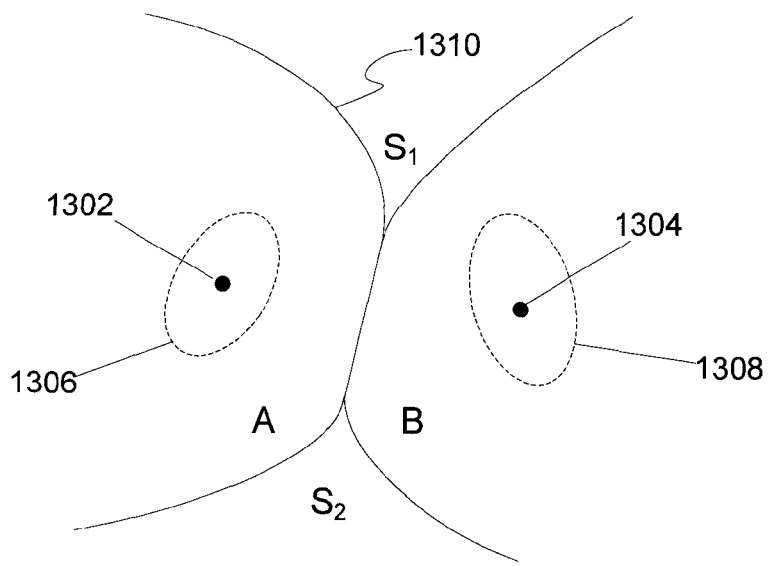
FIG. 13 illustrates the introduction of an artificial class, S having a location parameter equal to the overall mean and a covariance matrix equal to the covariance of the training vectors.
Figure 14:
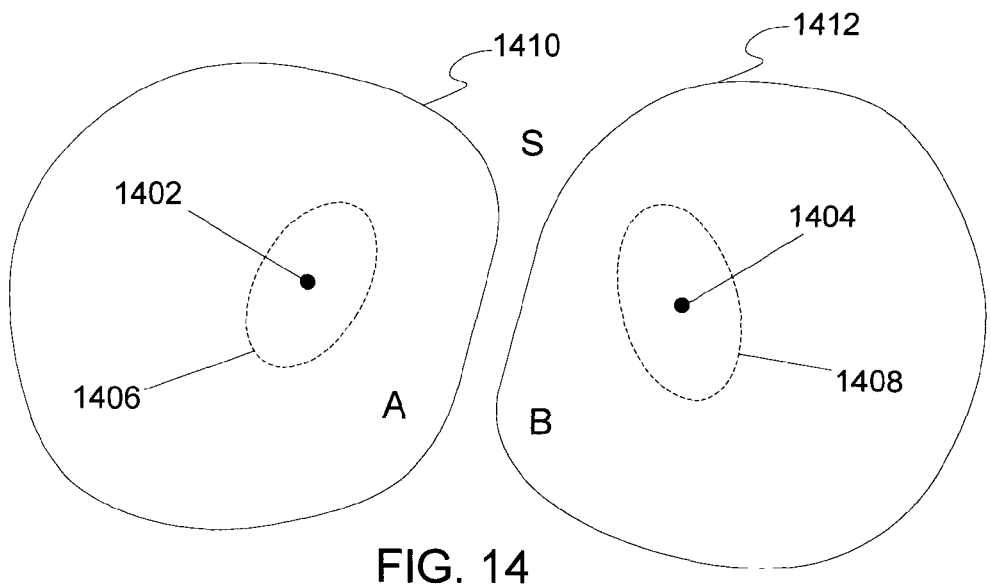
FIG. 14 illustrates the introduction of an artificial class, S having a location parameter equal to the overall mean and a covariance matrix equal to the covariance of the training vectors, with a relatively larger prior probability.

The effect of introducing an artificial class and adjusting its prior probability may be illustrated by the examples of FIGS. 12, 13, and 14. FIG. 12 depicts an example having two-dimensional feature vectors classified into two classes, A and B having Gaussian distributions. The location parameter 1202 and 95% ellipse 1206 for a class A, and the location parameter 1204 and 95% ellipse 1208 for a class B are shown. A decision boundary 1210 separates the space of feature vectors into two regions. Feature vectors to the left of the decision boundary are classified into class A, and feature vectors to the right of the decision boundary are classified into class B.

FIG. 13 illustrates the effect of introducing an artificial class, S, having a location parameter equal to the overall mean and a covariance matrix equal to the covariance of the training vectors. In this example, the artificial class is assigned a relatively small prior probability. The location parameter 1302 and 95% ellipse 1306 for a class A, and the location parameter 1304 and 95% ellipse 1308 for a class B are shown. A decision boundary 1310 separates the space of feature vectors into four regions. Feature vectors in the region labeled "A" are classified into class A, and feature vectors in the region labeled "B" are classified into class B. Feature vectors in the region labeled "$S_1$" or in the region labeled "$S_2$" are classified into the artificial class S.

FIG. 14 illustrates the effect of introducing an artificial class, S, having a location parameter equal to the overall mean and a covariance matrix equal to the covariance of the training vectors, with a relatively larger prior probability. The location parameter 1402 and 95% ellipse 1406 for a class A, and the location parameter 1404 and 95% ellipse 1408 for a class B are shown. In this example, two decision boundaries 1410, 1412 separate the space of feature vectors into three regions. Feature vectors in the region labeled "A" are classified into class A, and feature vectors in the region labeled "B" are classified into class B. Feature vectors in the region labeled "S" are classified into the artificial class S. Generally, as the prior probability of the artificial class is increased, more and more feature vectors will be classified into the artificial class. Because the feature vectors that get classified into the artificial class tend to be pulled from feature vectors having a low probability of membership in the other classes, the overall accuracy of classification should be improved.

In general, the choice of classifier type and the techniques used for constructing the artificial class are design implementation details that may be chosen with consideration of the particular details of the situation.

Figure 6:
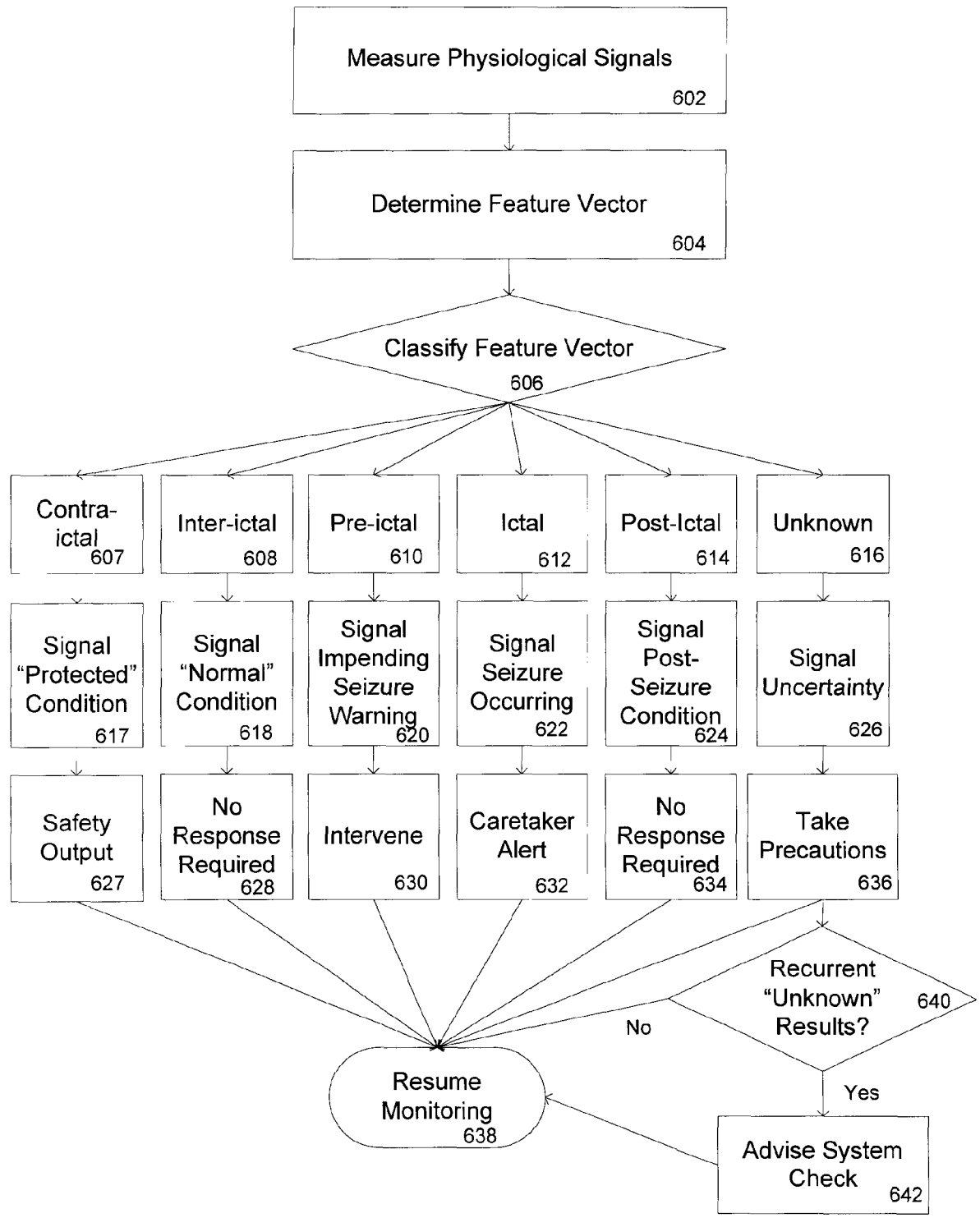
FIG. 6 is a flow chart for a seizure prediction system embodying aspects of the invention.

FIG. 6 is a flow chart for an embodiment of a seizure prediction system that embodies aspects of the invention. One or more physiological signals from a subject are measured 602. A feature vector is determined 604 from the measured signals, for example by a feature extractor described above. A classifier, employing an artificial class in accordance with the invention is applied to classify the feature vector 606. The result of the classification may be any of a number of defined classes associated with neurological states, such as contra-ictal 607, inter-ictal 608, pre-ictal 610, ictal 612, and post-ictal 614, or may be the artificial class associated with an unknown state 616. The classification may be used to generate a signal or to perform some action. The generation of the signal may cause storage of the classification in memory, activation of a user output, initiation of a therapy, or the like.

In one particular embodiment, the result of the classification may be signaled to a user 617, 618, 620, 622, 625, 626. Depending on the signal, the user may be informed that an indication of being "safe" is output 627, that no response is required 628, that intervention, such as for example medication or direct nerve stimulation, is recommended 630, an audible alarm may be issued to alert a caretaker 632, that no response is required 634, or, if the classification resulted in the artificial class, to take precautions 636, such as for example not driving or engaging in other potentially hazardous activities. In each case, the system may return to monitoring 638.

If monitoring results in recurrent classifications in the unknown class 640, the user may be advised that the system should be checked 642. Recurrent unknown results may be an indication that system parameters need adjustment, that retraining is desirable, or that some component of the system is malfunctioning.

Typically, systems such as those disclosed herein are able to store EEG signals from the subject. The stored EEG signals may thereafter be used to improve the classification provided by the classifier. Hence, over time, the classifier will be exposed to a larger number of feature vectors and will be able to better classify the subject. Thus, it is contemplated that the various classes will become more robust, while the artificial class would be reduced.

Figure 7:
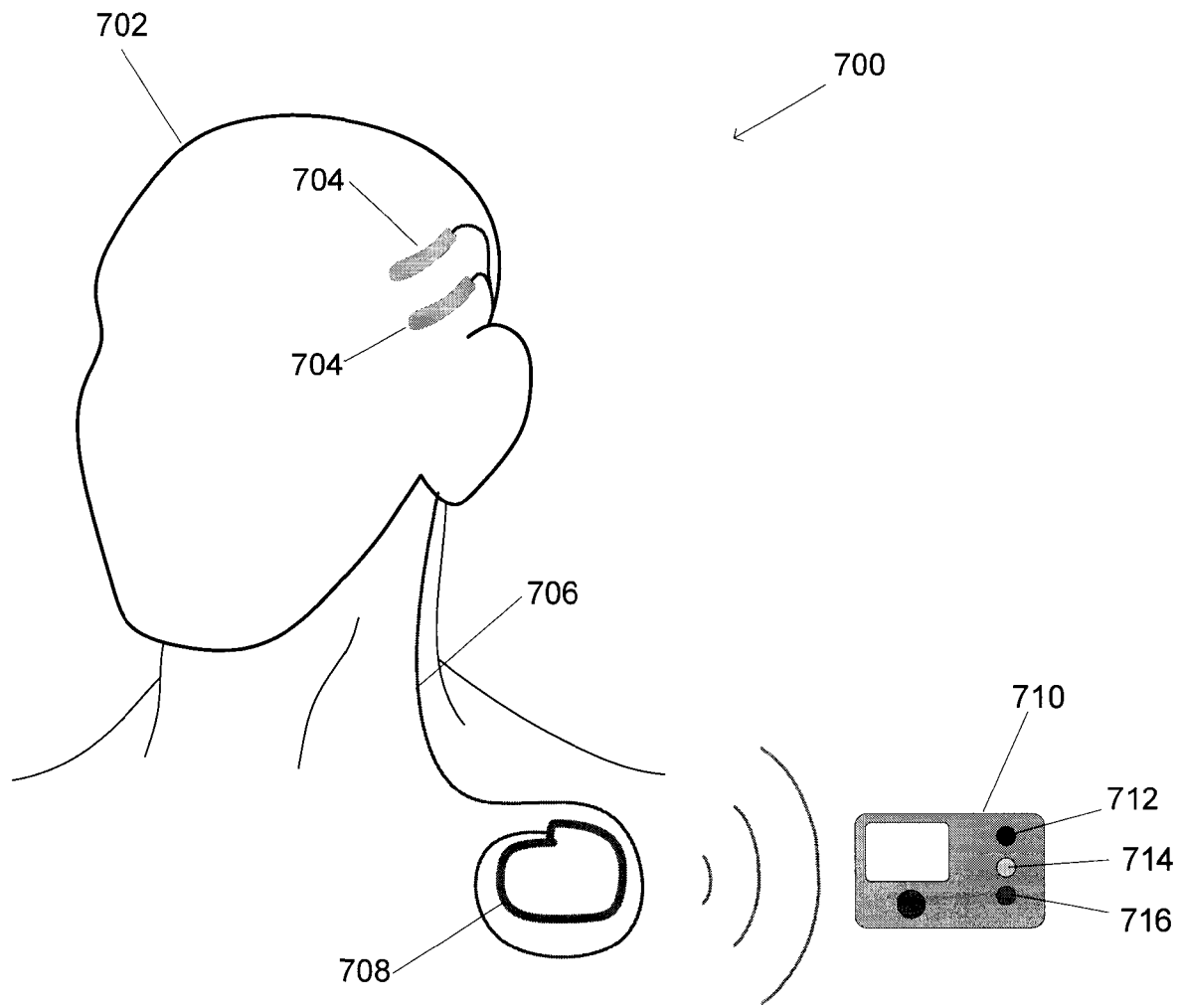
FIG. 7 is a simplified diagram of a system for monitoring a subject that may be configured in accordance with the systems and methods described herein.

FIG. 7 illustrates a system in which aspects of the invention may be embodied. The system 700 is used to monitor a subject 702 for purposes of measuring physiological signals and predicting neurological conditions. The system 700 of the embodiment provides for substantially continuous sampling of brain wave electrical signals such as in electroencephalograms or electrocorticograms, referred to collectively as EEGs.

The system 700 comprises one or more sensors 704 configured to measure signals from the subject 702. The sensors 704 may be located anywhere on the subject. In the exemplary embodiment, the sensors 704 are configured to sample electrical activity from the subject's brain, such as EEG signals. The sensors 704 may be attached to the surface of the subject's body (e.g., scalp electrodes), attached to the head (e.g., subcutaneous electrodes, bone screw electrodes, and the like), or, preferably, may be implanted intracranially in the subject 702. In one embodiment, one or more of the sensors 704 will be implanted adjacent a previously identified epileptic focus, a portion of the brain where such a focus is believed to be located, or adjacent a portion of a seizure network.

Any number of sensors 704 may be employed, but the sensors 704 will typically include between 1 sensor and 32 sensors, and preferably between about 4 sensors and about 16 sensors. The sensors may take a variety of forms. In one embodiment, the sensors comprise grid electrodes, strip electrodes and/or depth electrodes which may be permanently implanted through burr holes in the head. Exact positioning of the sensors will usually depend on the desired type of measurement. In addition to measuring brain activity, other sensors (not shown) may be employed to measure other physiological signals from the subject 702.

In an embodiment, the sensors 704 will be configured to substantially continuously sample the brain activity of the groups of neurons in the immediate vicinity of the sensors 704. The sensors 704 are electrically joined via cables 706 to an implanted communication unit 708. In one embodiment, the cables 706 and communication unit 708 will be implanted in the subject 702. For example, the communication unit 708 may be implanted in a subclavicular cavity of the subject 702. In alternative embodiments, the cables 706 and communication unit 708 may be attached to the subject 702 externally. In yet other embodiments, the sensors may be leadless (not shown) and may communicate directly with an external data device 710.

In one embodiment, the communication unit 708 is configured to facilitate the sampling of signals from the sensors 704. Sampling of brain activity is typically carried out at a rate above about 200 Hz, and preferably between about 200 Hz and about 1000 Hz, and most preferably at about 400 Hz. The sampling rates could be higher or lower, depending on the specific conditions being monitored, the subject 702, and other factors. Each sample of the subject's brain activity is typically encoded using between about 8 bits per sample and about 32 bits per sample, and preferably about 16 bits per sample.

In alternative embodiments, the communication unit 708 may be configured to measure the signals on a non-continuous basis. In such embodiments, signals may be measured periodically or aperiodically.

The external data device 710 is preferably carried external to the body of the subject 702. The external data device 710 receives and stores signals, including measured signals and possibly other physiological signals, from the communication unit 708. External data device 710 could also receive and store extracted features, classifier outputs, patient inputs, and the like. Communication between the external data device 710 and the communication unit 708 may be carried out through wireless communication. The wireless communication link between the external data device 710 and the communication unit 708 may provide a one-way or two-way communication link for transmitting data. The wireless communication link may be any type of wireless communication link, including but note limited to, a radiofrequency link, an infrared link, an ultrasonic link, inductive link, or the like.

In alternative embodiments, it may be desirable to have a direct communications link from the external data device 710 to the communication unit 708, such as, for example, via an interface device positioned below the subject's skin. The interface (not shown) may take the form of a magnetically attached transducer that would enable power to be continuously delivered to the communication unit 708 and would provide for relatively higher rates of data transmission. Error detection and correction methods may be used to help insure the integrity of transmitted data. If desired, the wireless data signals can be encrypted prior to transmission to the external data device 710.

Figure 8:
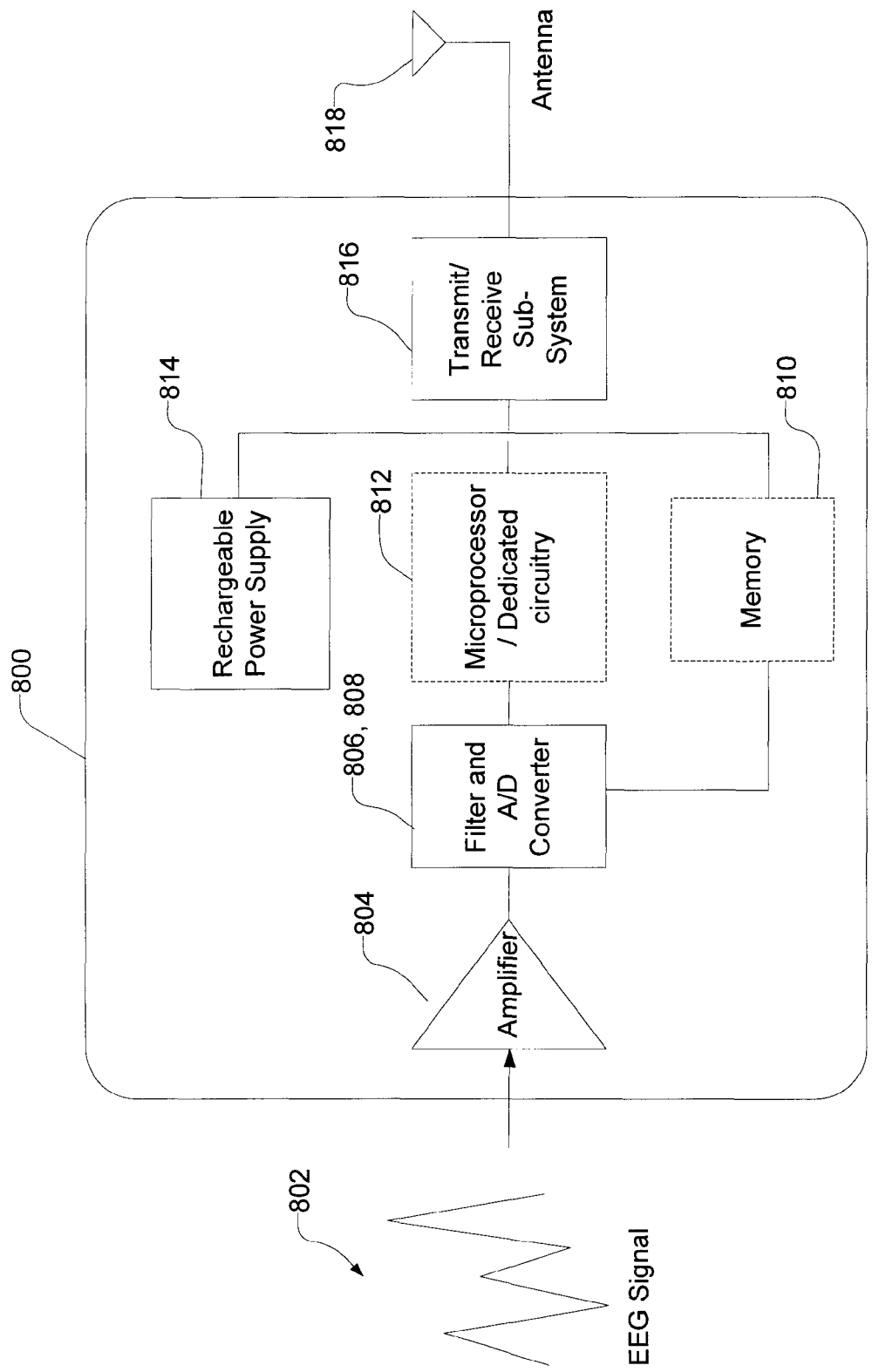
FIG. 8 is a block diagram of an implanted communication unit that may be used in accordance with the systems and methods described herein.

FIG. 8 depicts a block diagram of one embodiment of a communication unit 800 that may be used with the systems and methods described herein. Energy for the system is supplied by a rechargeable power supply 814. The rechargeable power supply may be a battery, or the like. The rechargeable power supply 814 may also be in communication with a transmit/receive subsystem 816 so as to receive power from outside the body by inductive coupling, radiofrequency (RF) coupling, and the like. Power supply 814 will generally be used to provide power to the other components of the implantable device. Signals 802 from the sensors 704 (FIG. 7) are received by the communication unit 800. The signals may be initially conditioned by an amplifier 804, a filter 806, and an analog-to-digital converter 808. A memory module 810 may be provided for storage of some of the sampled signals prior to transmission via a transmit/receive subsystem 816 and antenna 818 to the external data device 710 (FIG. 7). For example, the memory module 810 may be used as a buffer to temporarily store the conditioned signals from the sensors 704 (FIG. 7) if there are problems with transmitting data to the external data device 710 (FIG. 7), such as may occur if the external data device 710 experiences power problems or is out of range of the communications system. The external data device 710 can be configured to communicate a warning signal to the subject in the case of data transmission problems to inform the subject and allow him or her to correct the problem.

The communication unit 800 may optionally comprise circuitry of a digital or analog or combined digital/analog nature and/or a microprocessor, referred to herein collectively as "microprocessor" 812, for processing the signals prior to transmission to the external data device 710. The microprocessor 812 may execute at least portions of the analysis as described herein. For example, in some configurations, the microprocessor 812 may run one or more feature extractors 104a, 104b, 105 (FIG. 1) that extract characteristics of the measured signal that are relevant to the purpose of monitoring. Thus, if the system is being used for diagnosing or monitoring epileptic subjects, the extracted characteristics (either alone or in combination with other characteristics) may be indicative or predictive of a neurological condition. Once the characteristic(s) are extracted, the microprocessor 812 may transmit the extracted characteristic(s) to the external data device 710 and/or store the extracted characteristic(s) in memory 810. Because the transmission of the extracted characteristics is likely to include less data than the measured signal itself, such a configuration will likely reduce the bandwidth requirements for the communication link between the communication unit 800 and the external data device 710.

In some configurations, the microprocessor 812 in the communication unit 800 may comprise multiple cores and may run the one or more classifiers 106, 107 (FIG. 1), possibly on separate cores, as described above with respect to FIG. 1. The result 108 (FIG. 1) of the classification may be communicated to the external data device 710.

Figure 9:
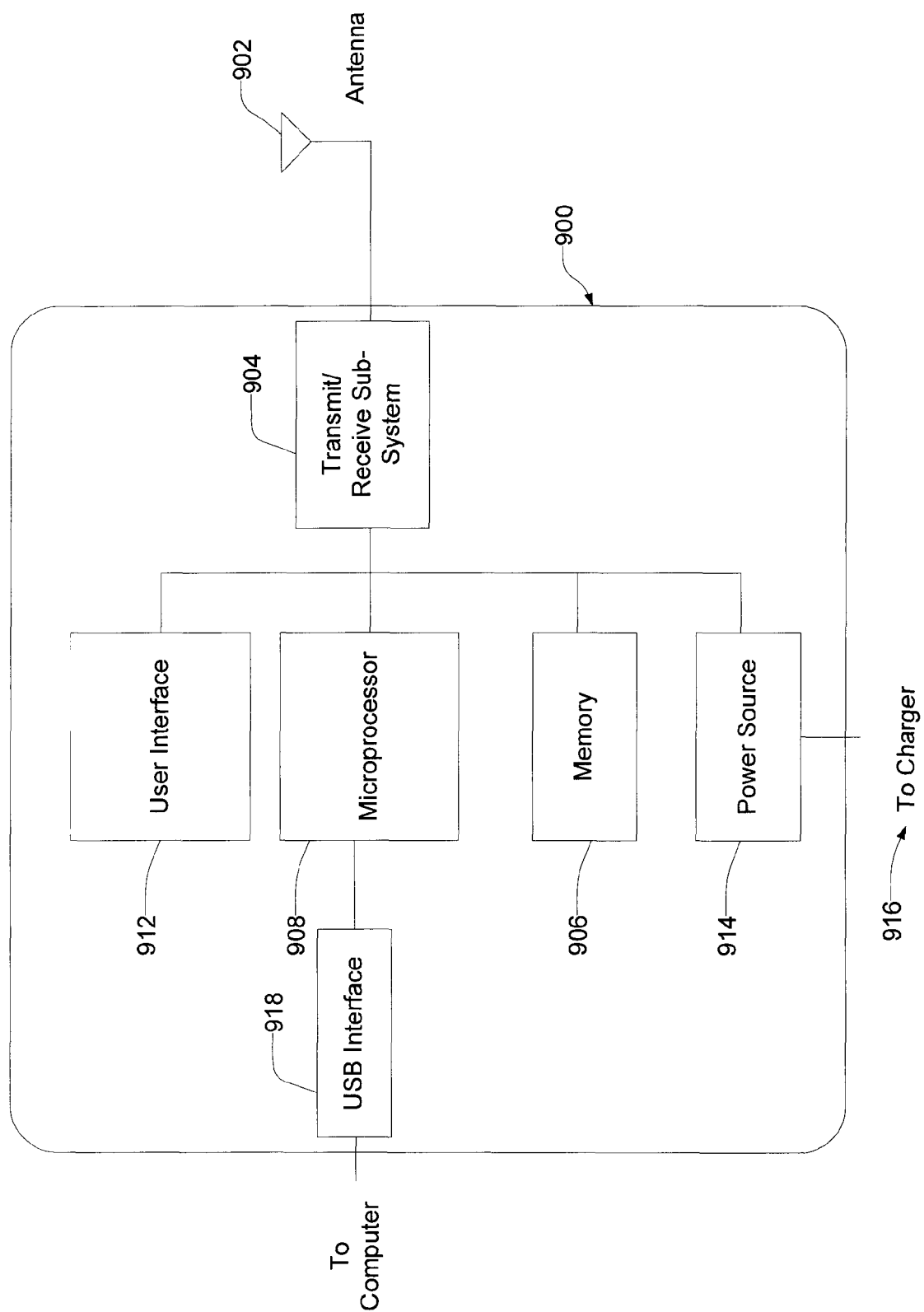
FIG. 9 is a block diagram of an external data device that may be used in accordance with the systems and methods described herein.

FIG. 9 provides a schematic diagram of some of the components that may be included in an external data device 900 which may also include any combination of conventional components. Signals from the communication unit 800 are received at an antenna 902 and conveyed to a transmit/receive subsystem 904. The signals received may include, for example, a raw measured signal, a processed measured signal, extracted characteristics from the measured signal, a result from analysis software that ran on the implanted microprocessor 812 (FIG. 8), or any combination thereof.

The received data may thereafter be stored in memory 906, such as a hard drive, RAM, EEPROM, removable flash memory, or the like and/or processed by a single core or multiple core microprocessor, application specific integrated circuit (ASIC) or other dedicated circuitry of a digital or analog or combined digital/analog nature, referred to herein collectively as a "microprocessor" 908. Microprocessor 908 may be configured to request that the communication unit 800 perform various checks (e.g., sensor impedance checks) or calibrations prior to signal recording and/or at specified times to ensure the proper functioning of the system.

Data may be transmitted from memory 906 to microprocessor 908 where the data may optionally undergo additional processing. For example, if the transmitted data is encrypted, it may be decrypted. The microprocessor 908 may also comprise one or more filters that filter out low-frequency or high-frequency artifacts (e.g., muscle movement artifacts, eye-blink artifacts, chewing, and the like) so as to prevent contamination of the measured signals.

External data device 900 will typically include a user interface for displaying outputs to the subject and for receiving inputs from the subject. The user interface will typically comprise outputs such as auditory devices (e.g., speakers) visual devices (e.g., LCD display, LEDs, and the like), tactile devices (e.g., vibratory mechanisms), or the like, and inputs, such as a plurality of buttons, a touch screen, and/or a scroll wheel.

Referring again to FIG. 7, in one embodiment, the external data device 710 includes a collection of colored LEDs or lights 712, 714, 716 to indicate to the subject his or her condition. For example, if the result of classification indicates a safe condition, such as a contra-ictal classification, a green light 716 may be displayed. If the classification results in an indication that a seizure may be likely or imminent, a red light 712 may be displayed and the subject is thereby warned to cease potentially hazardous activity and to intervene appropriately, such a through the automatic or manual administration of medication. If the classification results in the artificial class, indicating an unreliable or uncertain condition, a yellow light 714 is displayed. The subject 702 is thus warned that safety cannot be assured because the current neurological state is unknown. The user is thus cautioned to exercise an appropriate level of care, such as, for example, avoiding potentially hazardous activities while perhaps not necessarily intervening such as with medication.

While FIG. 7 shows a simple embodiment that uses three lights, a variety of other types of outputs may be provided to the patient. For example, it may be desirable to have a larger number of lights that provide a finer grade of the subject's condition. For example, a purple light or other colored light may be used to indicate the unknown class, while the yellow light may be used to indicate an increased propensity for a seizure and the red light may be used to indicate a seizure has been detected.

In yet other embodiments, the lights may have an even finer grade. For example, the lights may include an orange light and a yellow light that may be used to indicate different levels of susceptibility for seizure, while the red light may be used to indicate a seizure has been detected. For each of the different levels of susceptibility, the subject's physician may prescribe different therapies for treating the subject.

Alternative ways for communicating the classification results to the subject are also contemplated. For example, various audible and tactile signals, including possibly voice prompts, may be produced corresponding to some classification results or changes of classification. Appropriate textual warning messages may be displayed in some circumstances. The classification result may be used to trigger an automatic response, perhaps by interfacing with another device, when certain classification results are indicated.

Recurring results of classifications in the artificial group, indicating uncertainty or unreliability in the classification, may indicate a problem with some component of the device, or that the classifier is unable to accurately classify the subject's condition. In that situation, instruction may be provided to the subject to bring the device to a clinician for possible testing and adjustment. Modifications to some of the parameters of the classification system may be attempted to attempt to improve the classification effectiveness.

The user interface may be adapted to allow the subject to indicate and record certain events. For example, the subject may indicate that medication has been taken, the dosage, the type of medication, meal intake, sleep, drowsiness, occurrence of an aura, occurrence of a neurological condition, or the like. Such inputs may be used in conjunction with the measured EEG data to improve the analysis and classification.

The LCD display may be used to output a variety of different communications to the subject including, status of the device (e.g., memory capacity remaining), battery state of one or more components of system, whether or not the external data device 710 is within communication range of the communication unit 708, a warning (e.g., a neurological condition warning), a prediction (e.g., a neurological condition prediction), a recommendation (e.g., "take medicine"), or the like. It may be desirable to provide an audio output or vibratory output to the subject in addition to or as an alternative to the visual display on the LCD.

Referring again to FIG. 9, external data device 900 may also include a power source 914 or other conventional power supply that is in communication with at least one other component of external data device 900. The power source 914 may be rechargeable. If the power source 914 is rechargeable, the power source may optionally have an interface for communication with a charger 916. While not shown in FIG. 9, external data device 900 will typically comprise a clock circuit (e.g., oscillator and frequency synthesizer) to provide the time base for synchronizing the external data device 900 and the communication unit 800 (FIG. 8).

Referring again to FIG. 7, in a preferred embodiment, most or all of the processing of the signals received by the communication unit 708 is done in an external data device 710 that is external to the subject's body. In such embodiments, the communication unit 708 would receive the signals from subject and may or may not pre-process the signals and transmit some or all of the measured signals transcutaneously to an external data device 710, where the prediction of the neurological condition and possible therapy determination is made. Advantageously, such embodiments reduce the amount of computational processing power that needs to be implanted in the subject, thus potentially reducing energy consumption and increasing battery life. Furthermore, by having the processing external to the subject, the judgment or decision making components of the system may be more easily reprogrammed or custom tailored to the subject without having to reprogram the communication unit 708.

In alternative embodiments, the predictive systems disclosed herein and treatment systems responsive to the predictive systems may be embodied in a device that is implanted in the subject's body, external to the subject's body, or a combination thereof. For example, in one embodiment the predictive system may be stored in and processed by the communication unit 708 that is implanted in the subject's body. A treatment analysis system, in contrast, may be processed in a processor that is embodied in an external data device 710 external to the subject's body. In such embodiments, the subject's propensity for neurological condition characterization (or whatever output is generated by the predictive system that is predictive of the onset of the neurological condition) is transmitted to the external subject communication assembly, and the external processor performs any remaining processing to generate and display the output from the predictive system and communicate this to the subject. Such embodiments have the benefit of sharing processing power, while reducing the communications demands on the communication unit 708. Furthermore, because the treatment system is external to the subject, updating or reprogramming the treatment system may be carried out more easily.

In other embodiments, signals may be processed in a variety of ways in the communication unit 708 before transmitting data to the external data device 710 so as to reduce the total amount of data to be transmitted, thereby reducing the energy demands of the transmit/receive subsystem 816 (FIG. 8). Examples include: digitally compressing the signals before transmitting them; selecting only a subset of the measured signals for transmission; selecting a limited segment of time and transmitting signals only from that time segment; extracting salient characteristics of the signals, transmitting data representative of those characteristics rather than the signals themselves, and transmitting only the result of classification. Further processing and analysis of the transmitted data may take place in the external data device 710.

In yet other embodiments, it may be possible to perform some of the prediction in the communication unit 708 and some of the prediction in the external data device 710. For example, one or more characteristics from the one or more signals may be extracted with feature extractors in the communication unit 708. Some or all of the extracted characteristics may be transmitted to the external data device 710 where the characteristics may be classified to predict the onset of a neurological condition. If desired, external data device 710 may be customizable to the individual subject. Consequently, the classifier may be adapted to allow for transmission or receipt of only the characteristics from the communication unit 708 that are predictive for that individual subject. Advantageously, by performing feature extraction in the communication unit 708 and classification in an external device at least two benefits may be realized. First, the amount of wireless data transmitted from the communication unit 708 to the external data device 710 is reduced (versus transmitting pre-processed data). Second, classification, which embodies the decision or judgment component, may be easily reprogrammed or custom tailored to the subject without having to reprogram the communication unit 708.

In yet another embodiment, feature extraction may be performed external to the body. Pre-processed signals (e.g., filtered, amplified, converted to digital) may be transcutaneously transmitted from communication unit 708 to the external data device 710 where one or more characteristics are extracted from the one or more signals with feature extractors. Some or all of the extracted characteristics may be transcutaneously transmitted back into the communication unit 708, where a second stage of processing may be performed on the characteristics, such as classifying of the characteristics (and other signals) to characterize the subject's propensity for the onset of a future neurological condition. If desired, to improve bandwidth, the classifier may be adapted to allow for transmission or receipt of only the characteristics from the subject communication assembly that are predictive for that individual subject. Advantageously, because feature extractors may be computationally expensive and energy hungry, it may be desirable to have the feature extractors external to the body, where it is easier to provide more processing and larger power sources.

More complete descriptions of systems that may be used to embody the concepts of the present disclosure are described in commonly owned, copending U.S. patent application Ser.

Nos. 11/321,897, 11/321,898, 11/322,150, all filed on Dec. 28, 2005, the complete disclosures of which are incorporated herein by reference. For energy savings, the systems may embody some of the energy saving concepts described in commonly owned, copending patent application Ser. Nos. 11/616,788 and 11/616,793, filed Dec. 27, 2006, the complete disclosures of which are incorporated herein by reference.

Figure 10:
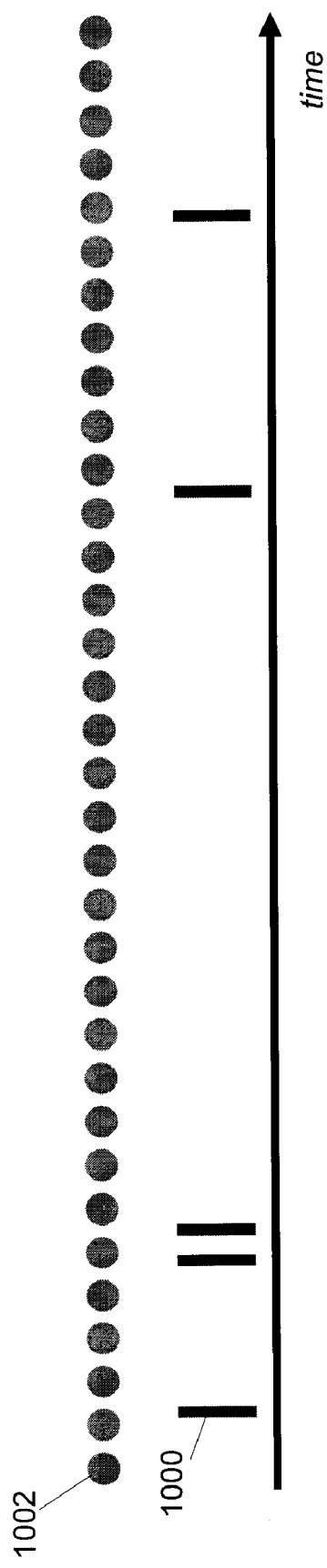
FIG. 10 is an example timeline for a typical therapeutic regimen for the treatment of epilepsy.

The ability to provide long-term low-power ambulatory measuring of physiological signals and prediction of neurological conditions can facilitate improved treatment regimens for certain neurological conditions. FIG. 10 depicts the typical course of treatment for a subject with epilepsy. Because the occurrence of neurological conditions 1000 over time has been unpredictable, present medical therapy relies on continuous prophylactic administration of anti-epileptic drugs ("AEDs"). Constant doses 1002 of one or more AEDs are administered to a subject at regular time intervals with the objective of maintaining relatively stable levels of the AEDs within the subject. Maximum doses of the AEDs are limited by the side effects of their chronic administration.

Figure 11:
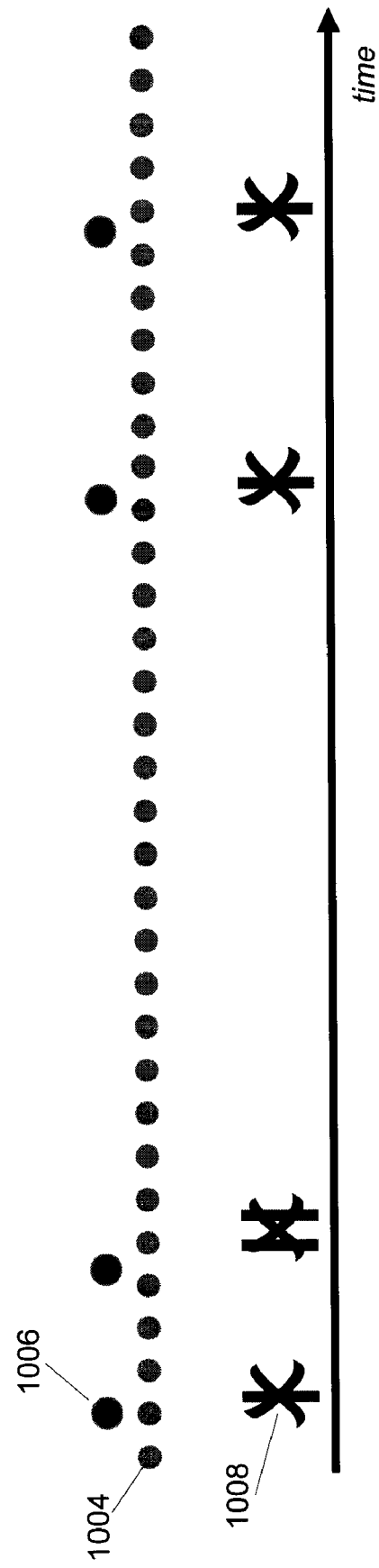
FIG. 11 is an example timeline for a therapeutic regimen for the treatment of epilepsy that may be enabled by the system and methods described herein.

Reliable long-term essentially continuously operating neurological condition prediction systems would facilitate acute epilepsy treatment. Therapeutic actions, such as, for example, brain stimulation, peripheral nerve stimulation (e.g., vagus nerve stimulation), cranial nerve stimulation (e.g., trigeminal nerve stimulation ("TNS")), or targeted administration of AEDs, could be directed by output from a neurological condition prediction system on an acute basis. One such course of treatment is depicted in FIG. 11, in which acute doses of an AED 1006 may be administered when it is determined that the subject is at an increased susceptibility to a seizure. Optionally, relatively lower constant doses 1004 of one or more AEDs may also be administered to a subject at regular time intervals in addition to or as an alternative to the acute administration of AEDs 1006. Medication doses 1006 are administered just prior to an imminent neurological condition 1008. By targeting the doses 1006 at the appropriate times, neurological conditions may be more effectively controlled and potentially eliminated 1008, while reducing side effects attendant with the chronic administration of higher levels of the AEDs.

While the present disclosure has been described in connection with various embodiments, illustrated in the various figures, it is understood that similar aspects may be used or modifications and additions may be made to the described aspects of the disclosed embodiments for performing the same function of the present disclosure without deviating therefrom. Other equivalent mechanisms to the described aspects are also contemplated by the teachings herein. For example, instead of generating an "unknown class," an equivalent classifier could utilize mathematical techniques that provide an "adaptive classification threshold." Such a threshold would achieve the same result as the "unknown class" without labeling the classifier output as "unknown", but would still achieve similar achievements in classification accuracy.

Furthermore, while the above focuses on classification for monitoring epileptic patients, the present invention is also applicable to other fields that analyze data for classification. Such areas include text recognition, speech recognition, image recognition, radar, targeting, data mining (as in retail analysis), communications (as in error detection and correction systems, speech recognition, spam filtering), and the like. Therefore, the present disclosure should not be limited to any single aspect, but rather construed in breadth and scope in accordance with the appended claims.

What is claimed:

1. A method of classification of a subject's neurological condition, the method comprising:
    identifying at least one class associated with an identified neurological condition; introducing an other class, the other class not being associated with an identified neurological condition;
    classifying a feature vector from a subject into an identified class or the other class; and
    generating a signal in response to classifying the feature vector.

2. The method as recited in claim 1, wherein identifying at least one class comprises processing feature vectors from a training data set to associate each processed feature vector with an identified class.

3. The method as recited in claim 1, wherein identifying at least one class comprises processing feature vectors from a training data set using unsupervised learning to identify at least one class.

4. The method as recited in claim 2, wherein introducing the other class comprises:
    generating artificial feature vectors; and
    associating the generated artificial feature vectors with the other class.

5. The method as recited in claim 4, wherein generating artificial feature vectors comprises randomly generating artificial feature vectors.

6. The method as recited in claim 5, wherein randomly generating artificial feature vectors comprises randomly generating artificial feature vectors according to a specified probability distribution.

7. The method as recited in claim 6, wherein the specified probability distribution has a mean and standard deviation substantially equal to the mean and standard deviation of the population of the feature vectors associated with the identified classes.

8. The method as recited in claim 1, wherein the other class is characterized by a probability density function.

9. The method as recited in claim 8, wherein identifying at least one class associated with an identified neurological condition comprises associating a probability density function with a class associated with an identified neurological condition.

10. The method as recited in claim 8, wherein identifying at least one class comprises processing feature vectors from a training data set to associate each processed feature vector with an identified class.

11. The method as recited in claim 8, wherein the probability density function represents a radial basis function.

12. The method as recited in claim 11, wherein the radial basis function represents a normal distribution.

13. The method as recited in claim 11, wherein the radial basis function represents a multiquadratic.

14. The method as recited in claim 11, wherein the radial basis function represents a thin plate spline.

15. The method as recited in claim 8, wherein the probability density function represents a uniform distribution.

16. The method as recited in claim 1, wherein the feature vector from a subject comprises at least one feature extracted from brain activity of the subject.

17. The method as recited in claim 1, wherein generating a signal in response to classifying a feature vector comprises providing an output to the subject indicative of a classification into the other class in response to a classification into the other class.

18. The method as recited in claim 1, wherein the at least one class comprises a class associated with a neurological condition selected from the group consisting of a pre-ictal condition and a pro-ictal condition.

19. The method as recited in claim 1, wherein the at least one class comprises a class associated with a contra-ictal condition.

20. The method as recited in claim 1, wherein the at least one class comprises a class associated with an inter-ictal condition.

21. The method as recited in claim 18, wherein the at least one class further comprises a second class associated with a contra-ictal condition.

* * * * *